United States Patent
Tsubouchi et al.

(10) Patent No.: US 10,646,147 B2
(45) Date of Patent: May 12, 2020

(54) SENSOR INSERTION DEVICE SET AND BASE PLATE

(71) Applicant: TERUMO KABUSHIKI KAISHA, Tokyo (JP)

(72) Inventors: Takeshi Tsubouchi, Yokosuka (JP); Eiji Arita, Hadano (JP); Hideyuki Momoki, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 197 days.

(21) Appl. No.: 15/648,003

(22) Filed: Jul. 12, 2017

(65) Prior Publication Data

US 2017/0303831 A1 Oct. 26, 2017

Related U.S. Application Data

(63) Continuation of application No. PCT/JP2015/005016, filed on Oct. 1, 2015.

(30) Foreign Application Priority Data

Jan. 27, 2015 (JP) .................................. 2015-013734

(51) Int. Cl.
*A61B 5/1455* (2006.01)
*A61B 5/1459* (2006.01)
(Continued)

(52) U.S. Cl.
CPC ........ *A61B 5/1459* (2013.01); *A61B 5/14503* (2013.01); *A61B 5/14546* (2013.01);
(Continued)

(58) Field of Classification Search
None
See application file for complete search history.

(56) References Cited

U.S. PATENT DOCUMENTS

| 2002/0171254 A1 | 11/2002 | McCormick |
| 2003/0133648 A1 | 7/2003 | Mitsuoka et al. |

(Continued)

FOREIGN PATENT DOCUMENTS

| EP | 2 327 984 A2 | 6/2011 |
| JP | 2008-506468 A | 3/2008 |

(Continued)

OTHER PUBLICATIONS

Chen et al, A two degree of freedom micro-gripper with grasping and rotating functions for optical fibers assembling, Review of Scientific Instrument, 2013, vol. 83.

(Continued)

*Primary Examiner* — Eric F Winakur
*Assistant Examiner* — Marjan Fardanesh
(74) *Attorney, Agent, or Firm* — Foley & Lardner LLP

(57) ABSTRACT

A sensor insertion assembly includes: a sensor insertion device comprising a needle member configured to be inserted in a living body together with a biological information sensor and to be pulled out of the living body after leaving a distal end side of the sensor in the living body; and a base plate detachably attached to a first end side of the sensor insertion device, the base plate comprising a clamp portion configured to move so as to clamp a proximal end side of the sensor extending to an outside of the living body after pulling out the needle member and along with an operation of detaching the sensor insertion device from the base plate.

12 Claims, 12 Drawing Sheets

(51) Int. Cl.
 A61B 5/145 (2006.01)
 A61B 5/00 (2006.01)
(52) U.S. Cl.
 CPC .......... *A61B 5/6833* (2013.01); *A61B 5/6849* (2013.01); *A61B 5/742* (2013.01); *A61B 5/14532* (2013.01); *A61B 2560/063* (2013.01); *A61M 2205/04* (2013.01); *A61M 2205/3306* (2013.01)

(56) References Cited

U.S. PATENT DOCUMENTS

| 2010/0099965 | A1* | 4/2010 | Jacobson | A61B 5/0084 |
| | | | | 600/342 |
| 2013/0060105 | A1 | 3/2013 | Shah et al. | |
| 2013/0267811 | A1 | 10/2013 | Pryor et al. | |
| 2014/0142405 | A1 | 5/2014 | Brister et al. | |

FOREIGN PATENT DOCUMENTS

| JP | 2011-224381 A | 11/2011 |
| JP | 2014-529481 A | 11/2014 |
| WO | WO-2006/017358 A1 | 2/2006 |
| WO | WO-2008/103972 A1 | 8/2008 |
| WO | WO-2014/162383 A1 | 10/2014 |

OTHER PUBLICATIONS

Dai et al, Packaging of optical fibers using microfabricated nickel clamps, Jm3 Letters, Jan.-Mar. 2008, vol. 7(1).
Extended European Search Report dated Jun. 8, 2018 in corresponding application No. 15879821.
International Search Report dated Dec. 28, 2015 in corresponding application No. PCT/JP2015/005016.
Liao et al, Acute Response in vivo of a Fiber-Optic Sensor for Continuous Glucose Monitoring from Canine Studies on Point Accuracy, Sensors, 2010, pp. 7789-7802.
Liao et al, Percutaneous fiber-optic sensor for chronic glucose monitoring in vivo, Biosensors and Bioelectronics, 2008, pp. 1458-1465.
Translation of the Written Opinion of the International Searching Authority dated Dec. 28, 2015 in corresponding application No. PCT/JP2015/005016.
International Search Report issued in International Patent Application No. PCT/JP2015/005016 dated Dec. 28, 2015.

* cited by examiner

SENSOR INSERTION DEVICE SET AND BASE PLATE

CROSS-REFERENCE TO RELATED APPLICATIONS

The present application is a bypass continuation of PCT Application No. PCT/JP2015/005016, filed on Oct. 1, 2015, which claims priority to Japanese Application No. 2015-013734, filed on Jan. 27, 2015, the contents of which are hereby incorporated by reference in their entireties.

BACKGROUND

The present disclosure relates to a sensor insertion assembly (also referred to as a "device set") including a sensor insertion device and a base plate, and to the base plate for such a sensor insertion assembly. The sensor insertion device is configured to insert a sensor that detects biological information of a living body, such as a patient, into the living body.

It is known to insert or embed a sensor in a body of a person to be measured, such as a patient, and detect an analyte (for example, glucose, pH, cholesterol, protein, etc.) in blood or body fluid of the patient by using the sensor. In this case, a sensor insertion device is used for quickly and easily disposing the sensor through the skin of the patient (see JP 2011-224381 A).

An analyte measurement system (sensor insertion assembly) described in Patent Literature 1 includes an applicator (sensor insertion device) and an attachment unit to be left on the living body surface side with the sensor. In addition, the applicator of JP 2011-224381 A includes an insertion needle to be inserted with the sensor and a plunger sub-assembly (movement mechanism) that moves the sensor and the insertion needle to perform puncture.

SUMMARY

After leaving the sensor in the living body, the sensor is sometimes moved in a direction in which the sensor is pulled out of the living body due to a body movement of the person to be measured or the like. In this case, there is a possibility that correct biological information cannot be detected.

To address this, embodiments described herein aim to provide a sensor insertion assembly and a base plate capable of making the sensor left in the living body less likely to move in the pulling-out direction even with the body movement.

According to one embodiment, a sensor insertion assembly includes a sensor insertion device including a needle member that is to be inserted in a living body together with a sensor capable of detecting biological information and is to be pulled out of the living body after leaving a distal end side of the sensor in the living body, and a base plate detachably attached to a first end side of the sensor insertion device, and the base plate includes a clamp portion that moves so as to clamp a proximal end side of the sensor extending to an outside of the living body after pulling out the needle member and along with an operation of detaching the sensor insertion device from the base plate.

According to one aspect, the clamp portion includes a pair of leaf spring portions that clamp the proximal end side of the sensor, and the sensor insertion device is detachable from the base plate by being relatively rotated with respect to the base plate and includes a cam portion capable of changing an engagement relationship with the pair of leaf spring portions along with an operation of the rotating and thereby changing an amount of elastic deformation of the pair of leaf spring portions.

According to one aspect, the pair of leaf spring portions include a first leaf spring and a second leaf spring disposed so as to oppose the first leaf spring and having a larger spring constant than the first leaf spring, and the base plate includes a position regulating portion that regulates a position of the second leaf spring when being detached from the sensor insertion device.

According to one aspect, an adhesive portion that adheres on a surface of the living body is provided on a surface of the base plate opposing the surface of the living body.

According to one aspect, the sensor includes a detection portion that is to be left in the living body and is capable of detecting biological information and an optical fiber to a distal end portion of which the detection portion is attached and which is to be left in the living body so as to extend to the outside of the living body.

According to another embodiment, a base plate is configured to be detachably attached to a sensor insertion device that accommodates a needle member that is to be inserted in a living body together with a sensor capable of detecting biological information and is to be pulled out of the living body after leaving a distal end side of the sensor in the living body, and includes a clamp portion that moves so as to clamp a proximal end side of the sensor extending to an outside of the living body after pulling out the needle member and along with an operation of relatively rotating the base plate with respect to the sensor insertion device in a state of being attached to the sensor insertion device.

According to embodiments described herein, a sensor insertion assembly and a base plate capable of making a sensor left in a living body less likely to move in a pulling-out direction even with body movement can be provided.

DETAILED DESCRIPTION

Exemplary embodiments of a sensor insertion assembly and a base plate will be described below with reference to FIGS. 1 to 12. Members common to drawings are denoted with the same reference signs.

Figure 1:
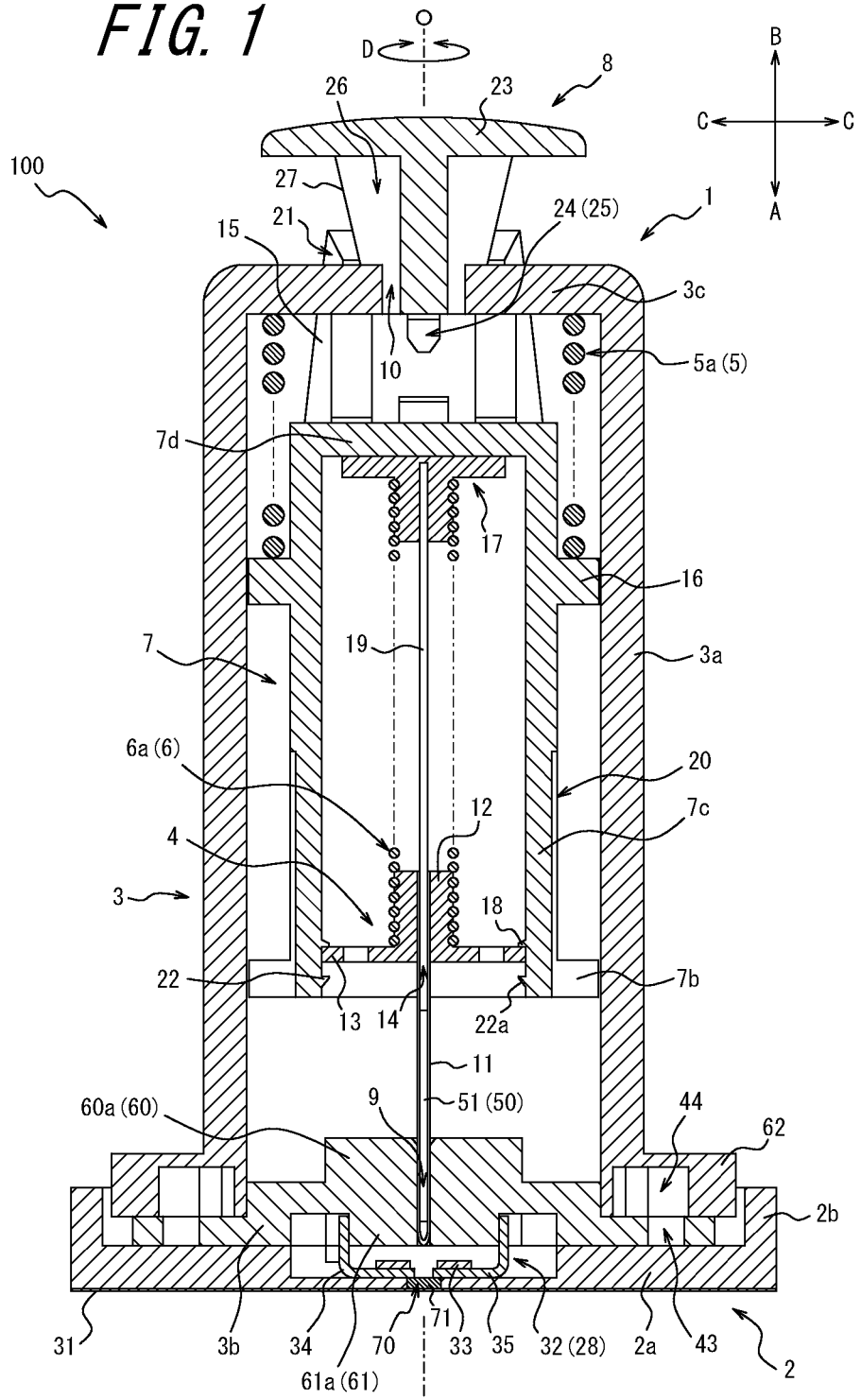
FIG. 1 is a section view of a sensor insertion assembly according to one embodiment, and illustrates a state before inserting a sensor and a needle member in a living body.
Figure 2:
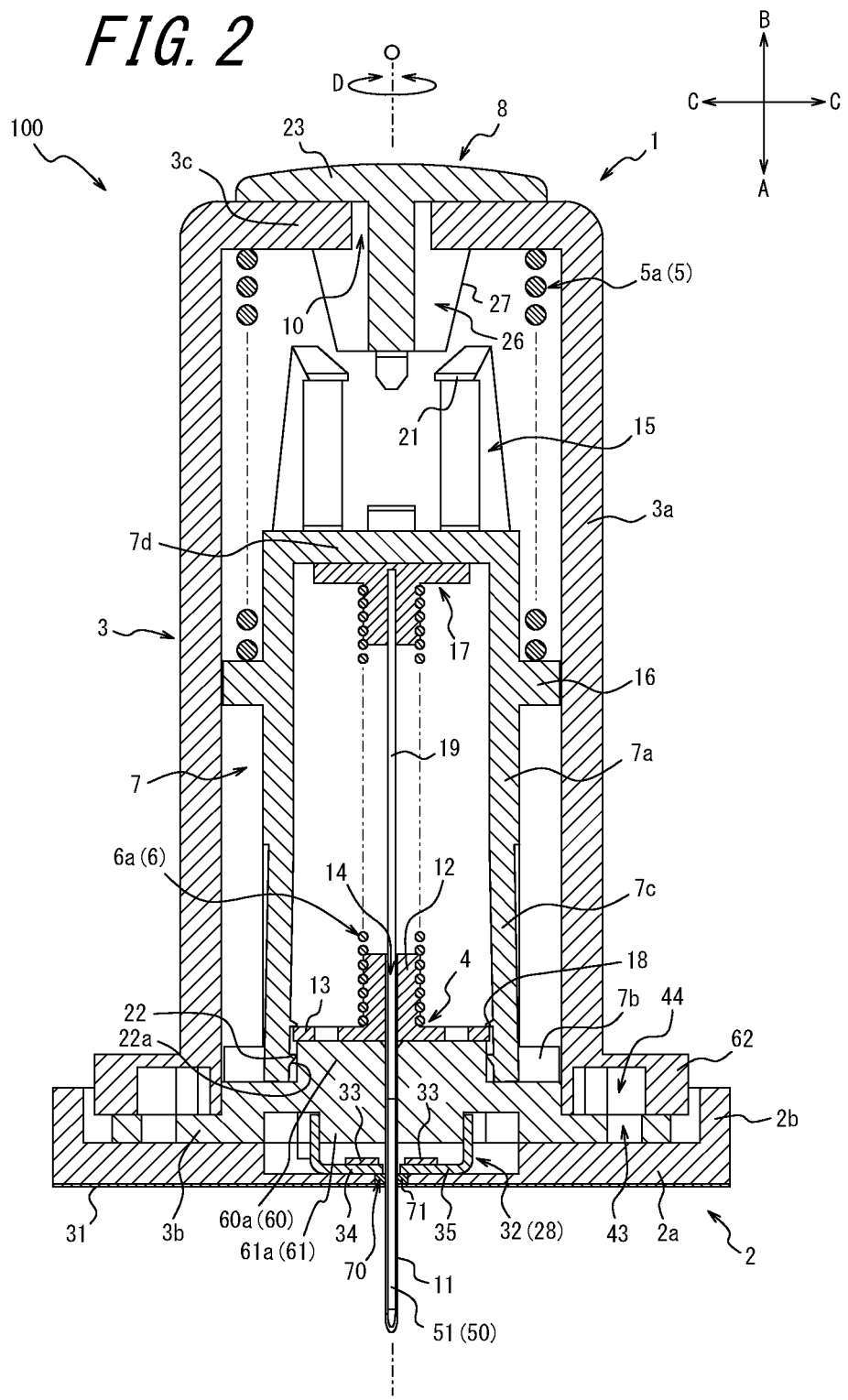
FIG. 2 illustrates a state in which the sensor and the needle member are moved to a position at which the sensor and the needle member can be inserted in the living body after the state illustrated in FIG. 1.
Figure 3:
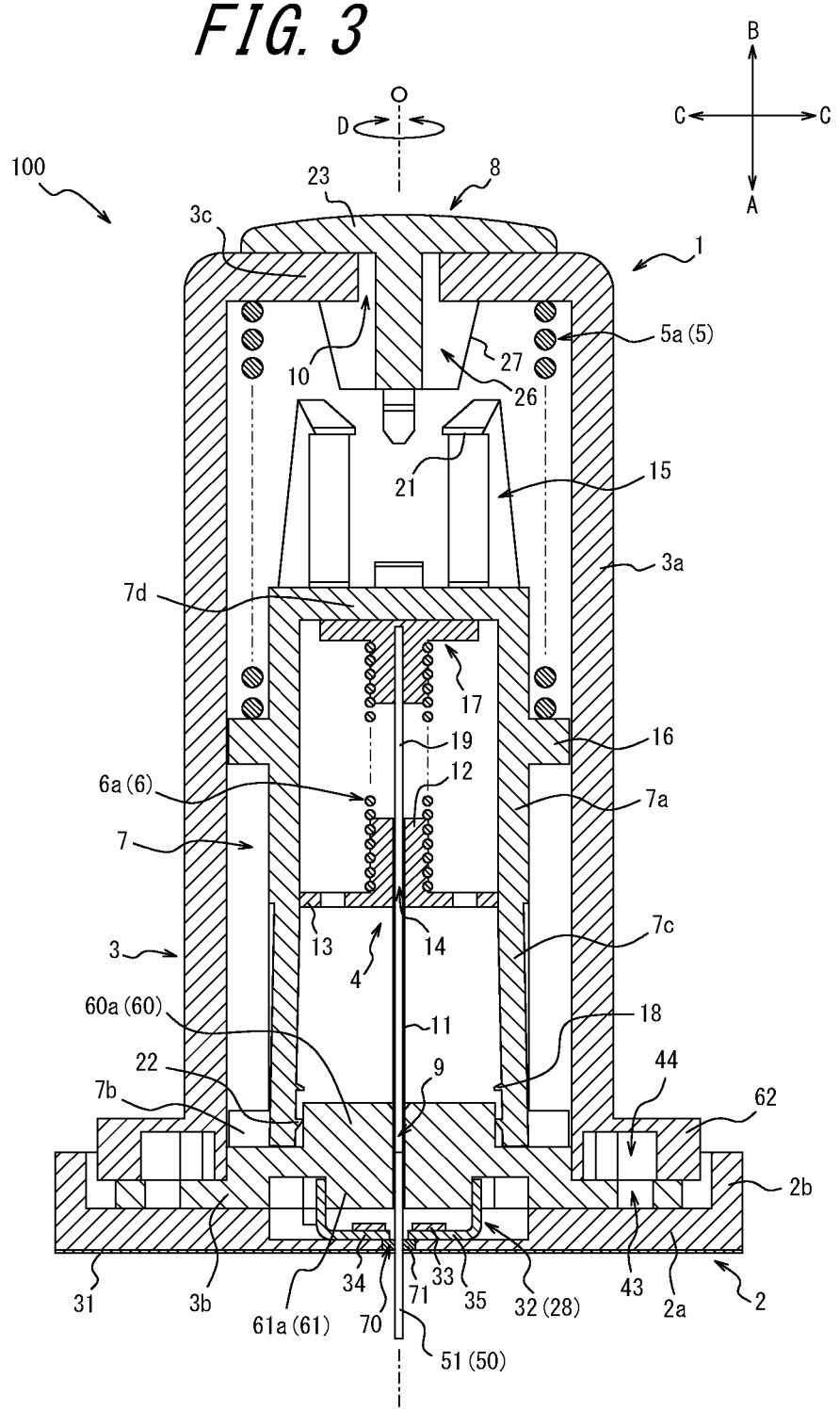
FIG. 3 illustrates a state in which the needle member is moved to a position at which the needle member can be pulled out of the living body after the state illustrated in FIG. 2.
Figure 4:
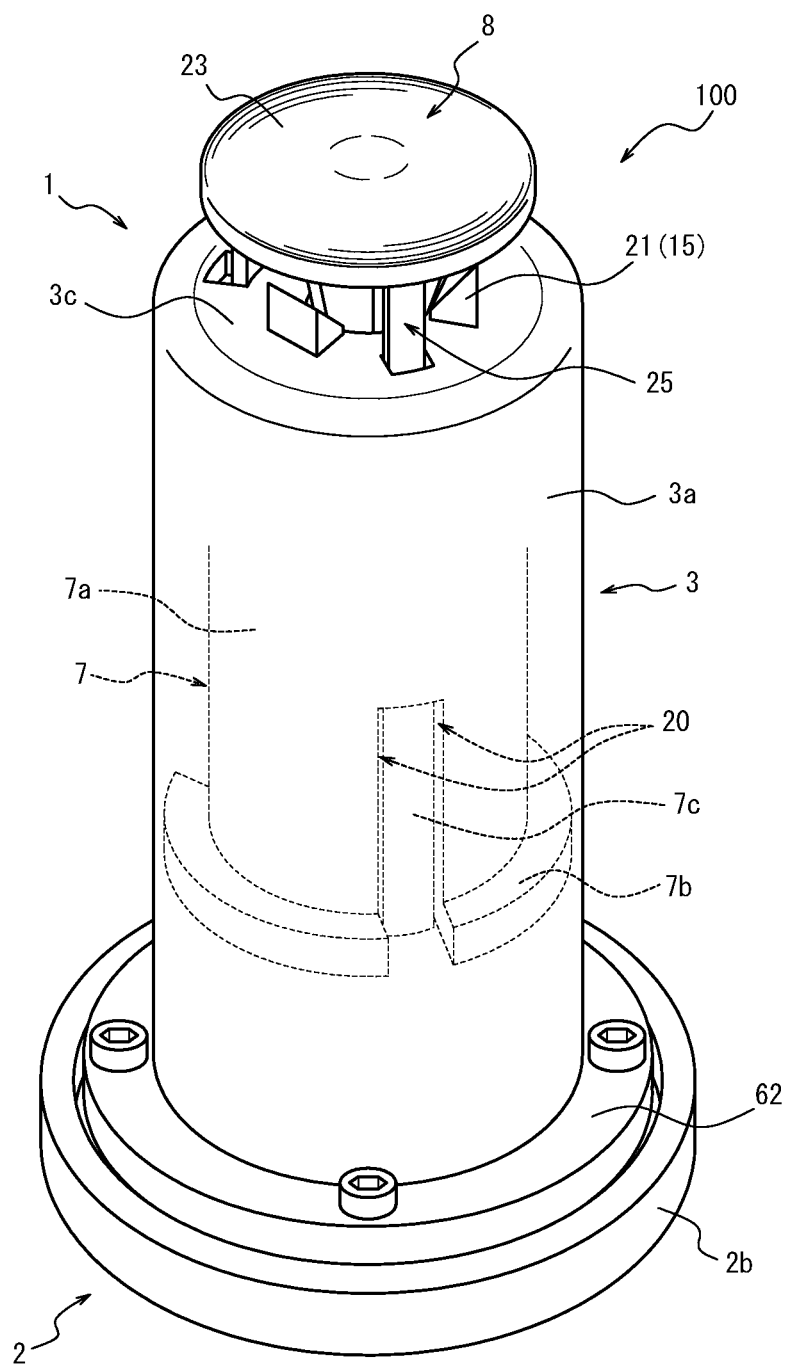
FIG. 4 is a perspective view of the sensor insertion assembly illustrated in FIG. 1.

FIGS. 1 to 3 are section views of a sensor insertion assembly 100 serving as an exemplary embodiment of the sensor insertion assembly illustrating the configuration thereof. In addition, FIG. 4 is a perspective view of the sensor insertion assembly 100. The sensor insertion assembly 100 includes a sensor insertion device 1 and a base plate 2 serving as an exemplary embodiment of the base plate detachably attached to a first end side of the sensor insertion device 1.

The sensor insertion assembly 100 inserts a sensor 50 in a living body through a lower surface (a surface on the lower side in FIGS. 1 to 4) of the base plate 2 by operating the sensor insertion device 1 with the base plate 2 placed on or pressed against the surface of the living body.

<Sensor Insertion Assembly 100>
<Sensor Insertion Device 1>

First, the sensor insertion device 1 in the sensor insertion assembly 100 will be described. As illustrated in FIGS. 1 to 4, the sensor insertion device 1 in the present exemplary embodiment inserts the sensor 50, which is capable of detecting biological information from body fluid, in a living body. Specifically, the sensor insertion device 1 includes a housing 3, a needle member 4, a first urging member 5, a second urging member 6, a movable member 7, and an operation member 8.

Here, FIGS. 1 and 4 each illustrate the sensor insertion device 1 and the sensor insertion assembly 100 in a state before the sensor 50 and the needle member 4 are inserted in the living body, and FIG. 2 illustrates the sensor insertion device 1 and the sensor insertion assembly 100 in a state in which the sensor 50 and the needle member 4 is moved to a position at which the sensor 50 and the needle member 4 can be inserted in the living body. In addition, FIG. 3 illustrates the sensor insertion device 1 and the sensor insertion assembly 100 in a state in which the needle member 4 is moved to a position at which the needle member 4 can be pulled out of the living body after the sensor 50 is left in the living body.

Each component of the sensor insertion device 1 according to the present exemplary embodiment and a characteristic portion constituted by each component will be described in detail below.

[Housing 3]

As illustrated in FIGS. 1 to 4, the housing 3 includes a cylinder portion 3a defining a hollow portion having a substantially cylindrical shape, a bottom plate portion 3b provided on a first end side (the lower side in FIGS. 1 to 4) of the cylinder portion 3a, and a top plate portion 3c provided on a second end side (the upper side in FIGS. 1 to 4) of the cylinder portion 3a. The bottom plate portion 3b is positioned at a first end side of the hollow portion defined by the cylinder portion 3a, and a through hole 9 through which a needle portion 11 of the needle member 4 that will be described later is movable is defined therein. In addition, the top plate portion 3c is positioned at a second end side of the hollow portion defined by the cylinder portion 3a, and a through hole 10 through which the movable member 7 is movable is defined therein.

The bottom plate portion 3b of the housing 3 includes an engagement portion 60 serving as a locking release portion configured to fit inside a cylinder portion 7a having a cylindrical shape in the movable member 7 that will be described late and engages with a deformation portion 7c that will be described later to deform the deformation portion 7c to the outside in the radial direction. More specifically, the engagement portion 60 according to the present exemplary embodiment is a projection portion 60a formed in a columnar shape on the upper surface of the bottom plate portion 3b.

In addition, the bottom plate portion 3b of the housing 3 includes a cam portion 61 capable of changing the amount of elastic deformation of a pair of leaf spring portions 32 by changing an engagement relationship between the base plate 2 and the pair of leaf spring portions 32 that will be described later along with an operation of relatively rotating with respect to the base plate 2. More specifically, the cam portion 61 according to the present exemplary embodiment is a projection portion 61a formed in an elliptical columnar shape on the lower surface of the bottom plate portion 3b.

The cylinder portion 3a and the top plate portion 3c of the housing 3 according to the present exemplary embodiment are constituted by a cylindrical housing body, and the bottom plate portion 3b according to the present exemplary embodiment is constituted by a bottom plate member attached and fixed to the housing body. Examples of a material for the housing body and the bottom plate member constituting the housing 3 include a resin material. Examples of the resin material include thermoplastic resins used for injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluorine resin, polycarbonate, polyamide, acetal resin, acrylic resin, and polyethylene terephthalate, and thermosetting resins such as phenol resin, epoxy resin, silicone resin, and unsaturated polyester.

[Needle Member 4]

As illustrated in FIGS. 1 to 4, the needle member 4 includes the needle portion 11 that is to be inserted in a living body with the sensor 50, a connection portion 12 positioned on the proximal end side of the needle portion 11 and connected to a retrieving spring 6a serving as the second urging member 6 that will be described later, and a locked portion 13 locked by a projection portion 18 serving as a locking portion of the movable member 7 that will be described later, and is movable in the housing 3 in a insertion direction A of the needle portion 11 and in a pulling-out direction B in which the needle portion 11 is pulled out of the living body.

Here, the insertion direction A of the needle portion 11 corresponds to a direction from the proximal end to the distal end of the needle portion 11 in the direction in which the needle portion 11 extends, and corresponds to a downward direction in FIGS. 1 to 4. By contrast, the pulling-out direction B of the needle portion 11 corresponds to a direction from the distal end to the proximal end of the needle portion 11 in the direction in which the needle portion 11 extends, and corresponds to an upward direction in FIGS. 1 to 4. The direction in which the needle portion 11 extends is the same direction as the direction of a center axis line of the needle portion 11 in the present exemplary embodiment. In addition, the insertion direction A may be described simply as "downward direction" and the pulling-out direction B may be described simply as "upward direction" below, and these mean the same thing defined herein.

The needle portion 11 of the present exemplary embodiment has a cylindrical external shape defining a hollow portion, and is capable of accommodating the sensor 50 in the hollow portion. The needle portion 11 is inserted in a living body with the sensor 50 accommodated in the hollow portion, and is pulled out of the living body after leaving the sensor 50 in the living body. The needle portion 11 of the present exemplary embodiment is constituted by a hollow cylindrical needle.

As a material for the hollow cylindrical needle constituting the needle portion 11, metal materials such as stainless steel, aluminum, aluminum alloy, titanium, and titanium alloy may be exemplarily used. In addition, a sharp cutting edge is formed in the distal end of the needle portion 11.

The connection portion 12 of the present exemplary embodiment has a substantially cylindrical shape in which a through hole 14 is defined, and a spiral groove in which the retrieving spring 6a serving as the second urging member 6 is locked is defined on the outer surface thereof.

The locked portion 13 of the present exemplary embodiment is a flange portion projecting from a lower end portion of the cylindrical connection portion 12 outward in the radial direction, and the needle member 4 is locked with respect to the movable member 7 as a result of an outer edge portion of the flange portion being engaged with and stopped by the projection portion 18 serving as a locking portion of the movable member 7. The details will be described later.

The connection portion 12 and the locked portion 13 of the present exemplary embodiment are constituted by a needle supporting member to which the hollow cylindrical needle constituting the needle portion 11 is fixed and which supports the hollow cylindrical needle. Specifically, the needle supporting member and the hollow cylindrical needle are engaged with each other such that an inner peripheral surface defining the through hole 14 of the connection portion 12 is in firm contact with the outer peripheral surface of a proximal end portion of the hollow cylindrical needle, and thus the hollow cylindrical needle is fixed to the needle supporting member.

The needle member is not limited to a needle member constituted by a hollow cylindrical needle and a needle supporting member as the needle member 4 of the present exemplary embodiment. For example, a needle portion, a connection portion, and a locked portion may be integrally formed as a single member. Further, a needle portion, a connection portion, and a locked portion may be constituted by three or more members.

As a material for the needle supporting member constituting the connection portion 12 and the locked portion 13, resin materials that can be used for the housing 3 described above, metal materials that can be used for the needle portion 11 described above, and so forth can be used.

[First Urging Member 5 and Second Urging Member 6]

The first urging member 5 is capable of urging the needle member 4 in the insertion direction A to move the needle member 4 to a first position (see FIG. 2) at which the needle portion 11 can be inserted in the living body. In addition, the second urging member 6 is capable of urging the needle member 4 in the pulling-out direction B to move the needle member 4 to a second position (see FIG. 3) at which the needle portion 11 that has reached the first position (see FIG. 2) can be pulled out of the living body.

The first urging member 5 and the second urging member 6 of the present exemplary embodiment are both elastic members (hereinafter an elastic member serving as the first urging member 5 will be described as "a first elastic member", and an elastic member serving as the second urging member 6 will be described as "a second elastic member"). Springs are used as the first elastic member and the second elastic member in the present exemplary embodiment. Hereinafter, the spring serving as the first elastic member will be simply described as "a insertion spring 5a", and the spring serving as the second elastic member will be simply described as "the retrieving spring 6a". Further, in the present exemplary embodiment, coil springs are used as the insertion spring 5a and the retrieving spring 6a.

Here, the first elastic member serving as the first urging member 5 and the second elastic member serving as the second urging member 6 of the present exemplary embodiment are arranged in series in the insertion direction A (or the pulling-out direction B). The movement of the needle member 4 in the insertion direction A (see FIGS. 1 and 2) is caused by an urging force of the first urging member 5 (in the present exemplary embodiment. An elastic force (restoring force) of the retrieving spring 6a serves as the second elastic member) without contribution of an urging force of the second urging member 6 (in the present exemplary embodiment, an elastic force (restoring force) of the insertion spring 5a serving as the first elastic member). In addition, the movement of the needle member 4 in the pulling-out direction B (see FIGS. 2 and 3) is caused by the urging force of the second urging member 6 without contribution of the urging force of the first urging member 5. The sensor insertion device 1 of the present exemplary embodiment includes a switching mechanism for realizing these operations. The switching mechanism will be described later.

[Movable Member 7]

The movable member 7 can be moved in the housing 3 in the insertion direction A by the urging force of the first urging member 5 (in the present exemplary embodiment, the elastic force of the insertion spring 5a that has been compressed). Specifically, the movable member 7 includes a locking claw portion 15 serving as a locking portion that is capable of engaging with the housing 3 in a state where the insertion spring 5a is compressed to a predetermined length and thus retaining the position of the movable member 7 with respect to the housing 3, and a receiving portion 16 that comes into contact with the insertion spring 5a serving as the first urging member 5 to be pressed in the insertion direction A.

As illustrated in FIGS. 1 to 3, the insertion spring 5a is disposed between the movable member 7 and the top plate portion 3c of the housing 3. And the insertion spring 5a can be compressed by moving the movable member 7 in the housing 3 in the pulling-out direction B against the elastic force of the insertion spring 5a. Then, the movable member 7 can be locked with respect to the housing 3 by engaging a claw 21 of the locking claw portion 15 with the top plate portion 3c of the housing 3 in a state where the insertion spring 5a is compressed between the movable member 7 and the housing 3 (see FIG. 1). That is, the movable member 7 is locked with respect to the housing 3 by the locking claw portion 15 in a state where the first urging member 5 retains energy (in the present exemplary embodiment, energy of the restoring force of the insertion spring 5a that has been compressed) to move the movable member 7 in the insertion direction A. Inclusion of such a structure enables compressing the insertion spring 5a in advance at the time of production. That is, inclusion of such a structure enables saving time and effort of a patient or a health care worker to charge the insertion spring 5a.

Then, the engagement between the housing 3 and the locking claw portion 15 of the movable member 7 is released by operating a pressing plate portion 23 of the operation member 8 that will be described later, and the movable member 7 is moved in the housing 3 in the insertion direction A by the elastic force of the insertion spring 5a pressing the receiving portion 16.

In addition, the needle member 4 is connected to the movable member 7 via the retrieving spring 6a serving as the second urging member 6, and the movable member 7 is capable of moving in the housing 3 in the insertion direction A due to the elastic force of the insertion spring 5a while retaining a state where the elastic force of the retrieving spring 6a expanded to a predetermined length is applied to the needle member 4. Specifically, the movable member 7 includes a connection portion 17 connected to an upper end portion of the retrieving spring 6a and the projection portion 18 serving as a locking portion that is capable of locking the needle member 4 connected to a lower end portion of the retrieving spring 6a in a state where the retrieving spring 6a is expanded to the predetermined length.

That is, the retrieving spring 6a is connected to the connection portion 12 of the needle member 4 and the connection portion 17 of the movable member 7, and is not connected to the housing 3. Accordingly, the movable member 7 can be moved in the insertion direction A by the elastic force of the insertion spring 5a while the state where the retrieving spring 6a is expanded to the predetermined length is retained by the projection portion 18.

Further, in the present exemplary embodiment, the movable member 7 is moved in the insertion direction A by the urging force (in the present exemplary embodiment, the elastic force of the insertion spring 5a) of the first urging member 5, and, when the needle member 4 reaches the first position (see FIG. 2), the locked state of the needle member 4 derived from the projection portion 18 is released by the engagement portion 60 of the housing 3 serving as a locking release portion. Accordingly, the needle member 4 is moved to the second position (see FIG. 3) in the pulling-out direction B by the urging force (in the present exemplary embodiment, the elastic force of the retrieving spring 6a) of the second urging member 6.

Further, the movable member 7 includes a rod portion 19 having a straight line shape and inserted in the needle portion 11 from the proximal end side of the needle portion 11 through the through hole 14 of the connection portion 12 of the needle member 4. This rod portion 19 presses the sensor 50 in the insertion direction A in the needle portion 11 when pulling out the needle portion 11 in a state where the sensor 50 is left in the living body after the needle portion 11 and the sensor 50 in the needle portion 11 are inserted in the living body. This prevents the sensor 50 from being pulled out together with the needle portion 11.

A detailed configuration of the movable member 7 of the present exemplary embodiment will be described below. The movable member 7 of the present exemplary embodiment includes a cylinder portion 7a having a cylindrical shape that surrounds the needle member 4 and the retrieving spring 6a serving as the second urging member 6, a flange portion 7b provided on a first end of on the lower side of the cylinder portion 7a so as to project outward in the radial direction, a leaf spring portion (see FIG. 4) serving as the deformation portion 7c that is positioned at an end portion of the cylinder portion 7a in the insertion direction A, is interposed in a cutout 20 in a circumferential direction D of the cylinder portion 7a, and is capable of being elastically deformed outward in the radial direction of the cylinder portion 7a, a top plate portion 7d provided at an end on the upper side of the cylinder portion 7a, the locking claw portion 15 that is provided on an upper surface of the top plate portion 7d so as to project in the pulling-out direction B and includes, at the distal end thereof, the claw 21 configured to engage with the top plate portion 3c of the housing 3, the receiving portion 16 that is provided on an outer surface of the cylinder portion 7a so as to project outward in the radial direction and comes into contact with the insertion spring 5a, the connection portion 17 which is provided below the top plate portion 7d and in the outer surface of which a spiral groove for locking the retrieving spring 6a is defined, and the rod portion 19 which extends from the connection portion 17 in the insertion direction A and a distal end portion of which is inserted in the needle portion 11 of the needle member 4.

As illustrated in FIGS. 1 to 3, the projection portion 18, serving as a locking portion described above, is formed on the inner wall of the deformation portion 7c and projects in a hollow portion defined by the cylinder portion 7a of the movable member 7. Therefore, the deformation portion 7c of the movable member 7 engages with the projection portion 60a having a columnar shape serving as the engagement portion 60 formed on the bottom plate portion 3b located at the end portion of the housing 3 in the insertion direction A and is elastically deformed so as to expand outward in the radial direction of the cylinder portion 7a when the needle member 4 reaches the first position (see FIG. 2). Accordingly, the projection portion 18 formed on the inner wall of the deformation portion 7c is also moved outward in the radial direction, and thus the locked state of the projection portion 18 serving as the locking portion of the movable member 7 and the flange portion serving as the locked portion 13 of the needle member 4 is released and the needle member 4 is moved in the cylinder portion 7a in the pulling-out direction B by the elastic force of the retrieving spring 6a (see FIG. 3).

Here, the outer diameter of the cylindrical projection portion 60a of the housing 3 is formed to be substantially equal to the inner diameter of the cylinder portion 7a of the movable member 7, and a projection 22, which converts a pressing force applied from the projection portion 60a in the pulling-out direction B into a pressing force outward in the radial direction of the cylinder portion 7a while sliding on the outer wall of the projection portion 60a when the projection portion 60a fits inside the cylinder portion 7a, is formed on the inner wall of the deformation portion 7c. Specifically, a lower surface 22a of the projection 22 is inclined with respect to a center axis line O (in the present exemplary embodiment, coincides with a center axis line of the needle portion 11) of the cylinder portion 7a such that the lower surface 22a approaches the center axis line O as the lower surface 22a advances in the pulling-out direction B, and the outer peripheral surface of the projection portion 60a elastically deforms the leaf spring portion serving as the deformation portion 7c outward in the radial direction while sliding on the lower surface 22a of the projection 22 (see FIG. 2, etc.).

The movement of the movable member 7 caused by the elastic force of the insertion spring 5a is configured so as to be guided in the insertion direction A as a result of the outer peripheral surfaces of the flange portion 7b and the receiving portion 16 of the movable member 7 sliding on the inner peripheral surface of the cylinder portion 3a of the housing 3. In addition, as illustrated in FIGS. 1 to 3, the rod portion 19 is surrounded by the retrieving spring 6a and extends from the connection portion 17 in the insertion direction A, and the distal end portion thereof reaches the needle portion 11 through the connection portion 12 of the needle member 4.

The cylinder portion 7a, the flange portion 7b, the deformation portion 7c, the top plate portion 7d, the locking claw portion 15, and the receiving portion 16 of the movable member 7 of the present exemplary embodiment are constituted by a single cylindrical body that has been formed as one piece. In addition, the connection portion 17 of the movable member 7 of the present exemplary embodiment is constituted by a connection member fastened to the top plate portion 7d of the cylindrical body by fastening means such as bolts or screws. Further, the rod portion 19 of the movable member 7 of the present exemplary embodiment is constituted by a rod member whose proximal end portion is fixed to the connection member constituting the connection portion 17. In the present exemplary embodiment, the connection member constituting the connection portion 17 includes a cylinder portion on the outer peripheral surface of which a spiral groove capable of locking the retrieving spring 6a is defined, and the proximal end portion of the rod member constituting the rod portion 19 is fixed with respect to the connection member in a state of being inserted in the cylinder portion of the connection member.

However, the above-described portions of the movable member are not limited to portions constituted by the cylinder body, the connection member and the rod member as the present exemplary embodiment. For example, all the portions of the movable member described above may be constituted by one or two members, or may be constituted by four or more members.

As an example of this, the cylinder body described above can be formed by connecting molded resin parts equally divided into three in the circumferential direction of the cylinder portion 7a via a connection method such as gluing or fusing. By using such a production method, complication of a mold can be suppressed.

Although three locking claw portions 15 are provided on the movable member 7 of the present exemplary embodiment, the number thereof is not limited to this and may be 1, 2, or 4 or more. Further, the shape and position of the locking claw portion 15 is not limited to the configuration of the present exemplary embodiment, and may be changed as appropriate. Further, the number, position, and shape of the leaf spring portion serving as the deformation portion 7c is not limited to the configuration of the present exemplary embodiment, and may be changed as appropriate in accordance with the number, position, and shape of engagement portions that deforms the deformation portion.

As a material for the cylinder body, connection member, and rod member constituting the movable member 7 of the present exemplary embodiment, resin materials that can be used for the housing 3 described above, metal materials that can be used for the needle portion 11 described above, and so forth can be used. However, it is preferable that the cylinder body is formed of a resin material that can be used for the housing 3 described above, and it is preferable that the connection member and the rod member are formed of metal materials that can be used for the needle portion 11 described above.

[Operation Member 8]

As illustrated in FIGS. 1 to 4, the operation member 8 of the present exemplary embodiment includes the pressing plate portion 23 of a circular plate shape configured to be operated by an user such as a patient or a health care worker, a projection portion 25 that includes a claw 24 that is formed on an lower surface of the pressing plate portion 23 and configured to be inserted in the housing 3 through the through hole 10 of the top plate portion 3c of the housing 3 and engage with a lower surface of the top plate portion 3c, and a pressing portion 26 that is formed on the lower surface of the pressing plate portion 23 and serves as a locking release portion capable of releasing the locked state of the movable member 7 with respect to the housing 3 by pressing and deforming the locking claw portion 15 of the movable member 7.

The claw 24 of the projection portion 25 is capable of engaging with the lower surface of the top plate portion 3c of the housing 3 such that the operation member 8 is not dropped as a result of being pulled out in the pulling-out direction B, and this suppresses pulling out and dropping of the operation member 8.

The pressing portion 26 includes a tapered portion 27 that is inclined with respect to the center axis line O of the cylinder portion 7a of the movable member 7 such that the tapered portion 27 approaches the center axis line O as the tapered portion 27 advances in the insertion direction A. When the pressing plate portion 23 is pressed down in the insertion direction A, moves in the insertion direction A with the pressing plate portion 23 through the through hole 10 of the top plate portion 3c. At this time, the tapered portion 27 of the pressing portion 26 presses the locking claw portion 15 of the movable member 7 outward in the radial direction of the cylinder portion 7a. Accordingly, the locking claw portion 15 deforms to the outside in the radial direction, and the engagement with the top plate portion 3c of the housing 3 is released. As a result of this, the engagement state of the movable member 7 with respect to the housing 3 is released.

As a material for the operation member 8 of the present exemplary embodiment, a resin material that can be used for the housing 3 described above can be used.

[Sensor 50 to Be Attached to Sensor Insertion Device 1]

Figure 5:
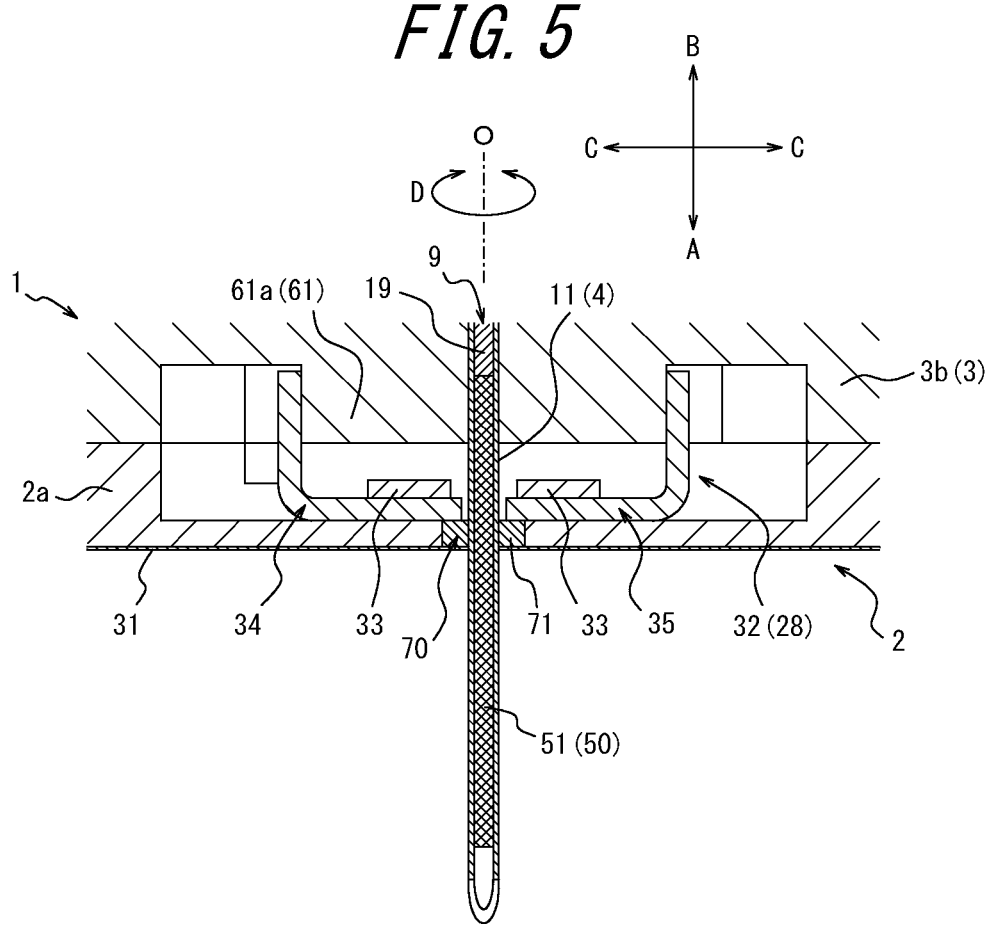
FIG. 5 is an enlarged section view in which the vicinity of the sensor and the needle portion is enlarged in the section view of the sensor insertion assembly illustrated in FIG. 2.
Figure 6:
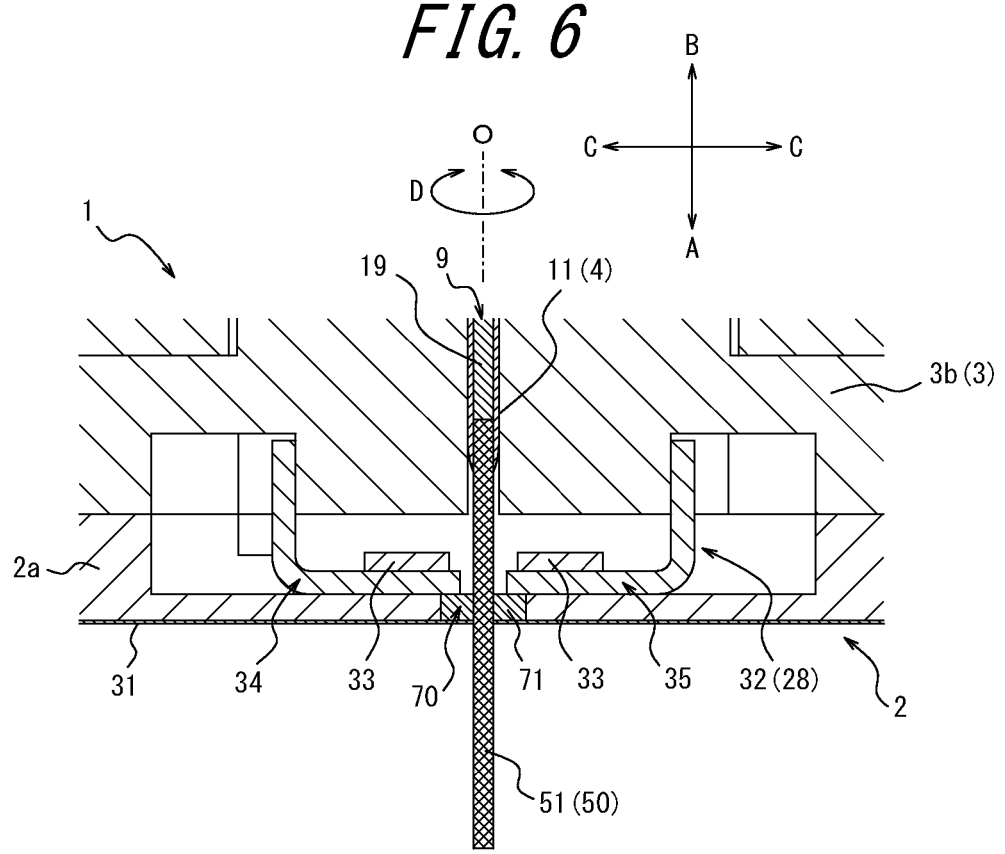
FIG. 6 is an enlarged section view in which the vicinity of the sensor and the needle portion is enlarged in the section view of the sensor insertion assembly illustrated in FIG. 3.

FIG. 5 is an enlarged section view of the vicinity of the needle portion 11 and the sensor 50 of the sensor insertion assembly 100 illustrated in FIG. 2, and FIG. 6 is an enlarged section view of the vicinity of the needle portion 11 and the sensor 50 of the sensor insertion assembly 100 illustrated in FIG. 3.

As illustrated in FIG. 5, the sensor 50 projects downward through an insertion hole 70 of the base plate 2 in a state of being accommodated in the hollow portion of the needle portion 11 that is constituted by a hollow cylindrical needle. Therefore, the sensor 50 and the needle portion 11 can be inserted in the living body by placing or pressing the lower surface of the base plate 2 of the sensor insertion assembly 100 in the state illustrated in FIG. 1 on or against the surface (skin) of the living body and operating the sensor insertion device 1 in this state to release the insertion spring 5a described above (see FIGS. 2 and 5). FIGS. 2 and 5 illustrate states where the needle member 4 is at the first position. In addition, a rubber member 71 serving as a septum which the needle portion 11 can pierce through and be pulled out through is fit in the insertion hole 70 of the base plate 2 of the present exemplary embodiment. This further suppresses the risk of bacteria or the like getting into the living body from the upper surface side of the base plate 2 through the insertion hole 70 of the base plate 2 and a puncture formed in the surface of the living body by the insertion of the needle portion 11 and causing infection.

The sensor 50 includes a detection portion (not illustrated) that is to be left in the living body and is capable of detecting biological information, and an optical fiber 51 to the distal end of which the detection portion is attached and which is to be left in the living body to extend to the outside of the living body, and the needle portion 11 is inserted in the living body in a state where both of the detection portion and the optical fiber 51 are accommodated in the hollow portion of the needle portion 11.

Then, in the state illustrated in FIG. 5, the elastic force of the retrieving spring 6a starts the movement of the needle member 4 in the pulling-out direction B due to an action of the switching mechanism that will be described later. However, as illustrated in FIG. 6, although the needle portion 11 moves in the pulling-out direction B, the sensor 50 does not move in the pulling-out direction B because the rod portion 19 presses the sensor 50. Thus, it becomes possible to leave the sensor 50 at a predetermined depth in the living body.

Further, after leaving the sensor 50 and pulling out the needle portion 11 by using the sensor insertion assembly 100, the sensor insertion device 1 is detached in a state where the base plate 2 is left on the living body side with the sensor 50. This enables connecting, to a portion of the optical fiber 51 of the sensor 50, which has been left, on the proximal end side that extends to the outside, a processing device constituted by an optical detection portion including an irradiation portion that irradiates the detection portion with excitation light and a light receiving portion that receives fluorescent light obtained from the detection portion in accordance with the amount of analyte, and a processing portion that processes signals obtained from the optical detection portion and the optical detection portion. Accordingly, the optical fiber 51 constitutes a transmission path through which the biological information detected by the detection portion is transmitted to the processing device. The processing device may be designed as appropriate in accordance with the object and use thereof, for example, as a memory that stores the biological information, a transmitter that transmits the biological information to an external device, or a display monitor that displays the biological information.

Although states where the sensor 50 is located in the needle portion 11 of the needle member 4 are shown for the sensor insertion device 1 of the present exemplary embodiment illustrated in FIGS. 1 to 3, the sensor 50 according to the present exemplary embodiment is not a constituent of the sensor insertion device 1 but a disposable item that can be detachably attached to the sensor insertion device 1 and used only once. Alternatively, the sensor maybe configured as a constituent of the sensor insertion device, and the whole of the sensor insertion device including the sensor may be configured as a disposable item. Further, although the needle member 4 of the present exemplary embodiment is configured to be undetachable from the sensor insertion device 1, the needle member may be detachable from the sensor insertion device and configured as a detachable unit that can be used as a disposable item.

In addition, although a sensor including an optical fiber is used as the sensor 50 in the present exemplary embodiment, a sensor that includes a lead connected to the detection portion left in the living body and extends to the outside of the living body and an electrical connection portion provided at a proximal end portion of the lead for connection with the processing device may be used. However, in the case where the sensor 50 including the optical fiber 51 as in the present exemplary embodiment is used, one having a cylindrical outer shape defining a hollow portion maybe used as the needle portion 11 of the needle member 4 because the electrical connection portion described above does not need to be provided. The needle portion 11 having such a cylindrical outer shape is easily produced compared with a U-shaped needle having a U-shape in cross section in which a gap is provided so as to let an electrical connection portion extend to the outside of the needle portion, and thus it is beneficial to be able to employ a needle portion having a circular shape in cross section as in the present exemplary embodiment.

[Switching Mechanism]

The sensor insertion device 1 of the present exemplary embodiment includes a switching mechanism that is capable of performing selective switching from moving the needle member 4 in the insertion direction A by the urging force (in the present exemplary embodiment, restoring force of the insertion spring 5a that has been compressed) of the first urging member 5 to moving the needle member 4 in the pulling-out direction B by the urging force (in the present exemplary embodiment, restoring force of the retrieving spring 6a that has been expanded) of the second urging member 6 when the needle member 4 reaches the first position (see FIG. 2).

Here, "selective switching" means that switching is performed such that the movement of the needle member 4 to the first position at the time of insertion and the movement of the needle member 4 to the second position at the time of pulling out are performed under the influence of different urging members. In the present exemplary embodiment, "selective switching" means that switching is performed between the movement of the needle member 4 at the time of insertion performed under the influence of the restoring force of the insertion spring 5a without the influence of the restoring force of the retrieving spring 6a and the movement of the needle member 4 performed at the time of pulling out performed under the influence of the restoring force of the retrieving spring 6a without the influence of the restoring force of the insertion spring 5a.

Specifically, the switching mechanism of the present exemplary embodiment is constituted by the projection portion 18 serving as a locking portion of the movable member 7 and the projection portion 60a having an columnar shape that is an engagement portion serving as a locking release portion of the housing 3.

As described above, the projection portion 18 serving as the locking portion of the movable member 7 is configured to lock the needle member 4 by retaining the state where the elastic force (restoring force) of the retrieving spring 6a that has been expanded is applied to the needle member 4, and is formed on the inner wall of the deformation portion 7c. In addition, the projection portion 60a serving as the locking release portion of the housing 3 is configured to release the locked state of the needle member 4 deriving from the projection portion 18 serving as the locking portion of the movable member 7 when the needle member 4 reaches the first position (see FIG. 2), and this projection portion 60a is formed on the bottom plate portion 3b and engages with the projection 22 of the deformation portion 7c to deform the deformation portion 7c to the outside in the radial direction when the needle member 4 reaches the first position. Accordingly, the needle member 4 is moved in the pulling-out direction B by the restoring force of the retrieving spring 6a without moving the movable member 7 in the housing 3, and is accommodated in the movable member 7, specifically, in the cylinder portion 7a of the movable member 7. In other words, the needle member 4 is moved to the second position (see FIG. 3) by the restoring force of the retrieving spring 6a.

The sensor insertion device 1 of the present exemplary embodiment is capable of automatically performing the insertion of the sensor 50 and the needle portion 11 in the living body by the urging force of the insertion spring 5a serving as the first urging member 5 and pulling-out of the needle portion 11 to the outside of the living body by the urging force of the retrieving spring 6a serving as the second urging member 6 in a coordinated manner without intervention of a manual operation by a user just performing an operation of pressing down the pressing plate portion 23 of the operation member 8, and thus is capable of shortening the time in which the needle portion 11 is present in the living body. Thus, the pain that the person to be measured in which the sensor 50 is to be left feels during a period from the insertion to the pulling-out of the needle portion 11 can be alleviated.

Further, because the sensor insertion device 1 of the present exemplary embodiment includes the switching mechanism described above, the urging force (in the present exemplary embodiment, elastic force of the retrieving spring 6a) of the second urging member 6 does not act so as to reduce the insertion speed in the insertion direction A at the time of inserting the sensor 50 and the needle portion 11, and, moreover, the urging force (in the present exemplary embodiment, elastic force of the insertion spring 5a) of the first urging member 5 does not act so as to reduce the pulling-out speed in the pulling-out direction B at the time of pulling out the needle portion 11. Accordingly, the sensor insertion device 1 of the present exemplary embodiment makes it easier to realize a configuration to accelerate the insertion speed of the sensor 50 and the needle portion 11 and the pulling-out speed of the needle portion 11 compared with a sensor insertion device that does not include a switching mechanism like the present exemplary embodiment, that is, a sensor insertion device in which the elastic force of a retrieving spring acts so as to reduce the insertion speed and the elastic force of a insertion spring acts so as to reduce the pulling-out speed.

<Base Plate 2>

Figure 7:
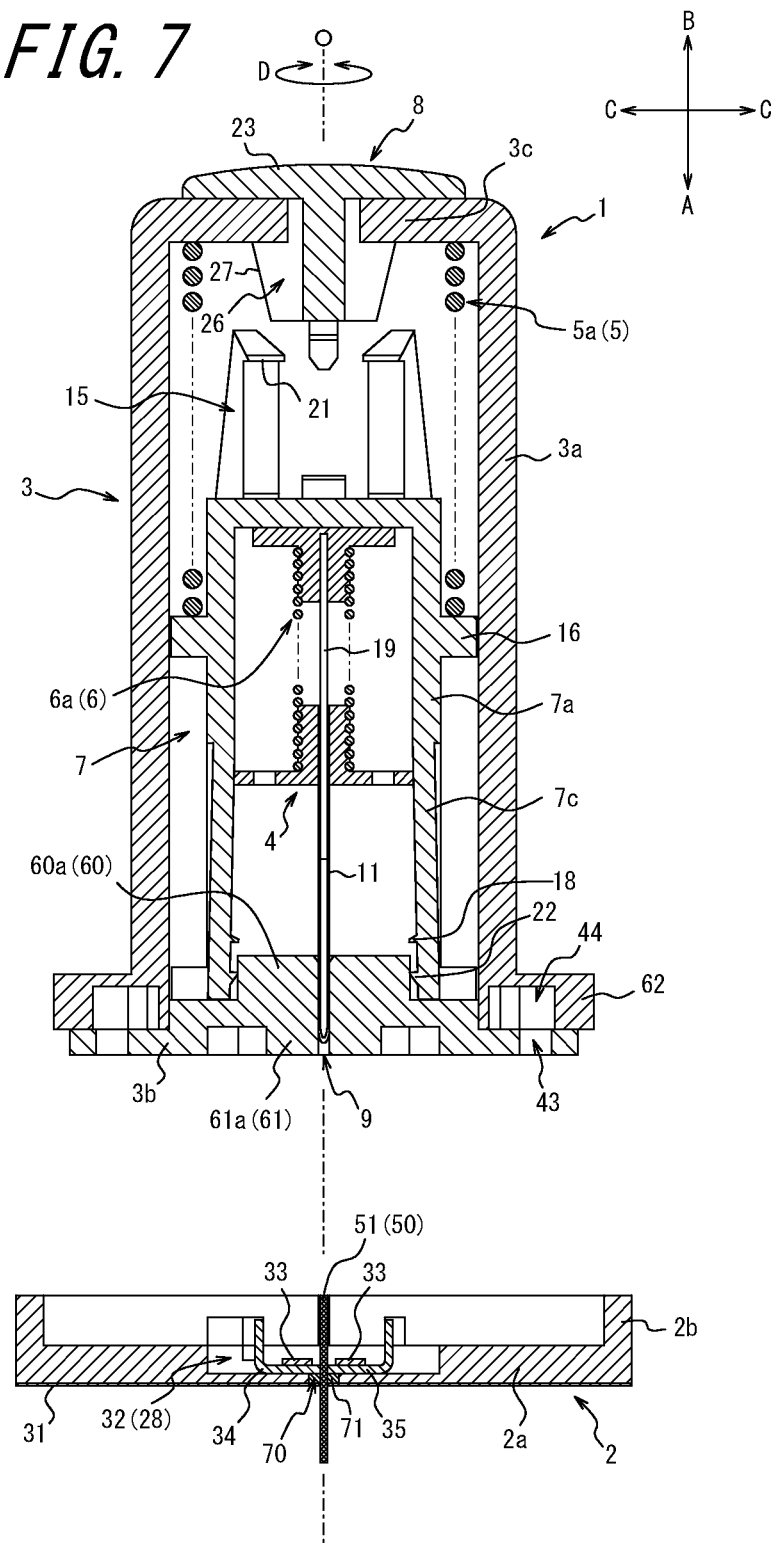
FIG. 7 illustrates a state in which a sensor insertion device and a base plate are separated from each other after the state illustrated in FIG. 3.

Next, the base plate 2 will be described. As described above, the sensor insertion assembly 100 includes the sensor insertion device 1 described above and the base plate 2 detachably attached to a first end of the sensor insertion device 1. FIG. 7 illustrates a state where the sensor insertion device 1 and the base plate 2 are separated by relatively rotating the sensor insertion device 1 and the base plate 2 with respect to each other after the state illustrated in FIG. 3.

The base plate 2 is used with the sensor insertion device 1 when inserting and leaving the sensor 50 in the living body (see FIGS. 1 to 3, etc.), and is separated from the sensor insertion device 1 and left on the living body side with the sensor 50 after leaving the sensor 50 in the living body (see FIG. 7).

The base plate 2 separated from the sensor insertion device 1 and left on the surface (skin) of the living body is used as a supporting member of the processing device. That is to say, the base plate 2 is a member to which the processing device connected to the proximal end portion of the optical fiber 51 of the sensor 50 can be attached.

In other words, the base plate 2 is detachably attached to the sensor insertion device 1 that accommodates the needle member 11 that is to be inserted in the living body with the biological information sensor 50 and pulled out of the living body after leaving the distal end side of the sensor 50 in the living body.

Figure 8:
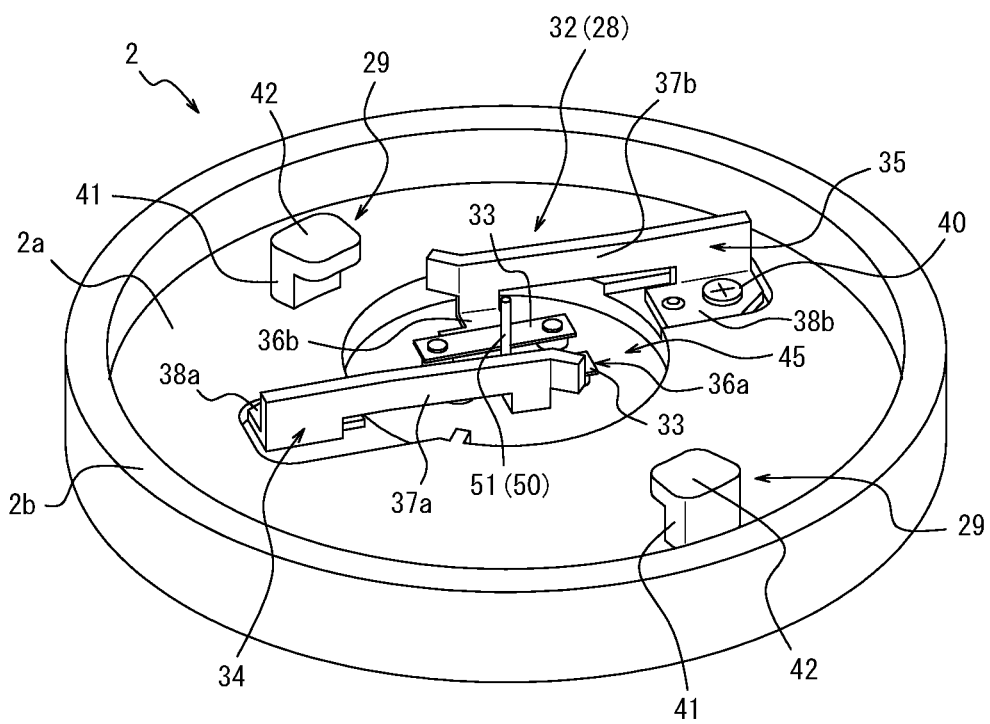
FIG. 8 is a perspective view of the sensor and the base plate illustrated in FIG. 7.
Figure 9:
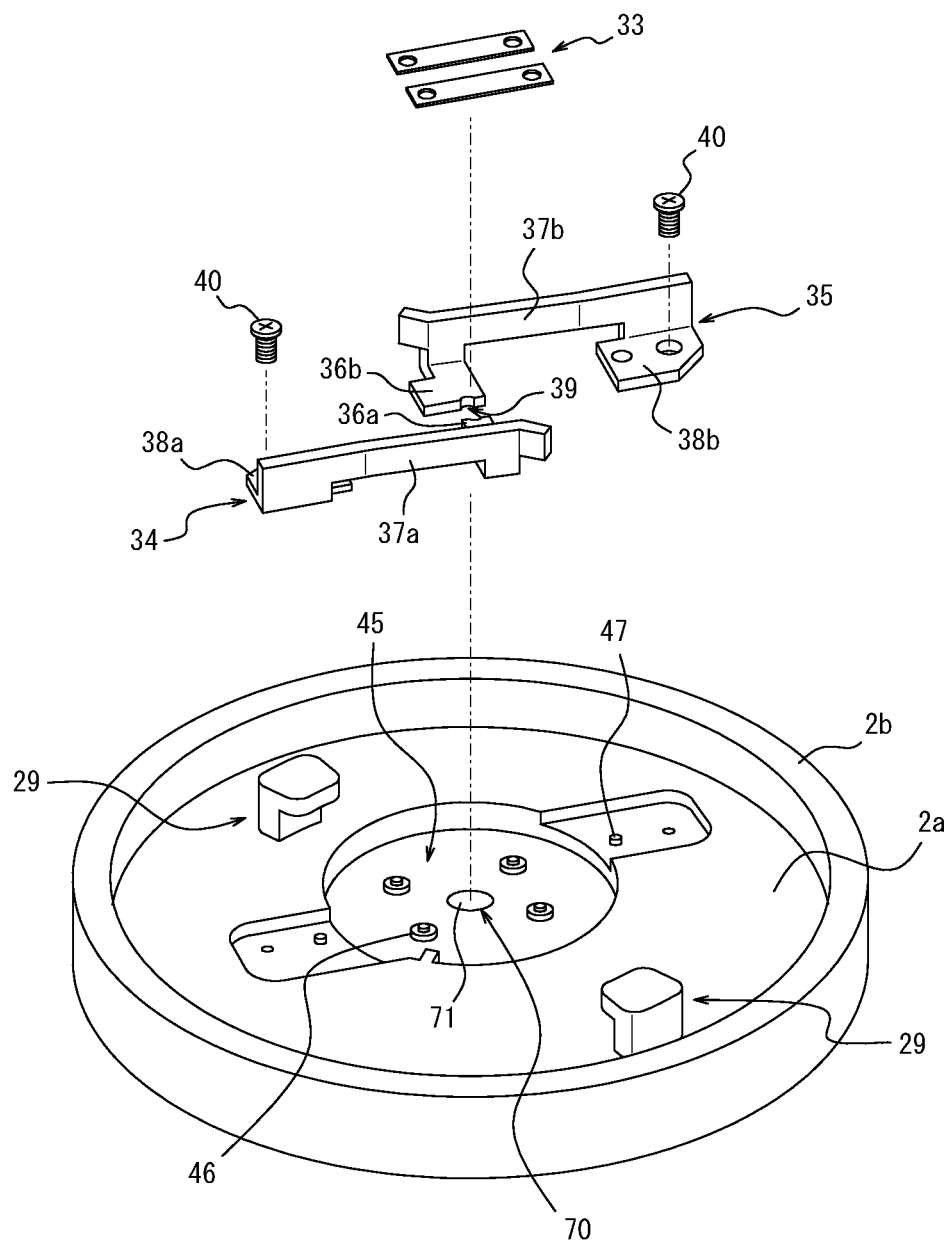
FIG. 9 is an exploded perspective view of the base plate illustrated in FIG. 8.

FIG. 8 is a perspective view of the sensor 50 and the base plate 2 in a state of being left on the living body side, and FIG. 9 is an exploded perspective view of the base plate 2.

Figure 10:
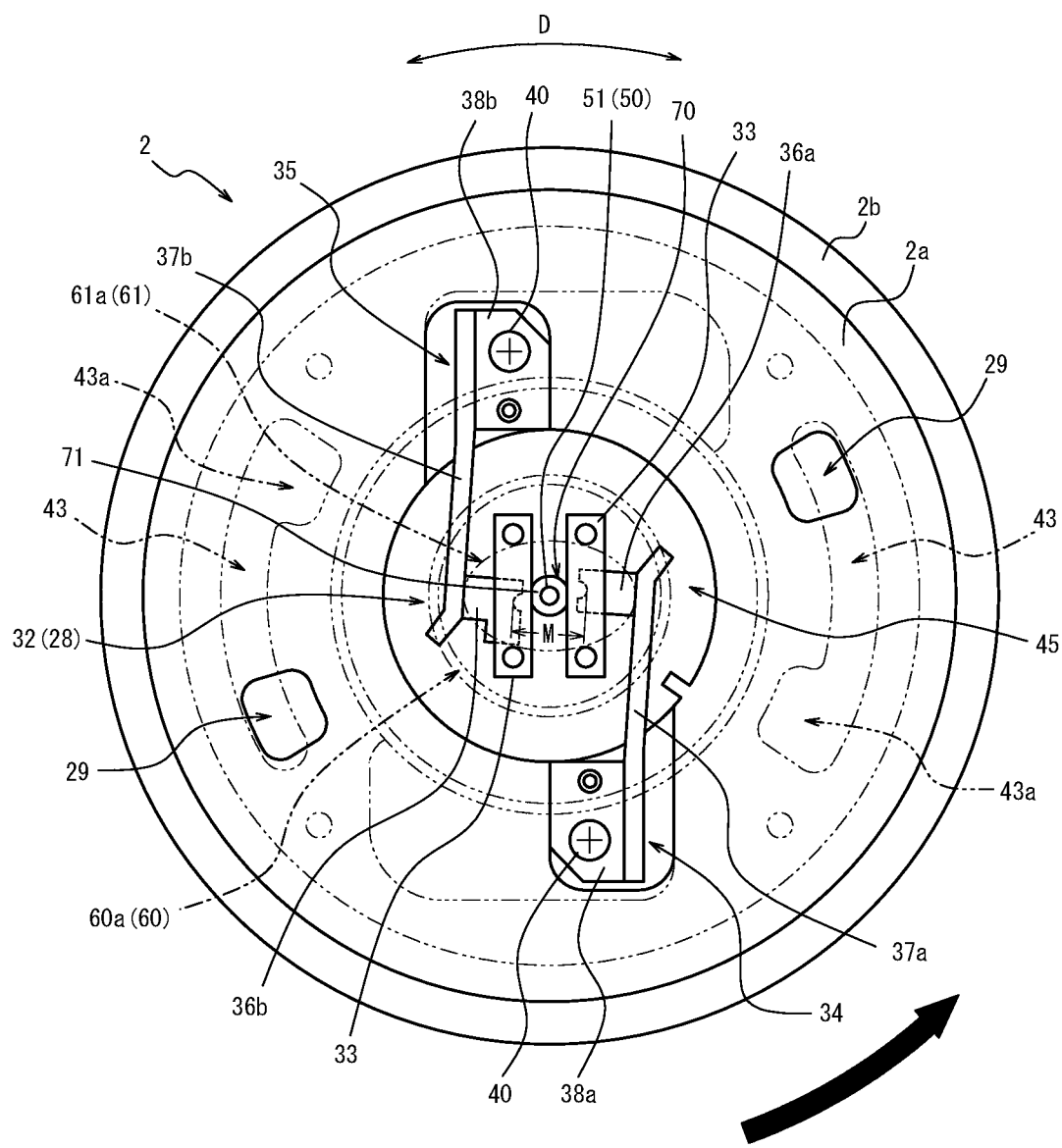
FIG. 10 illustrates an upper surface of the base plate attached to the sensor insertion device.
Figure 11:
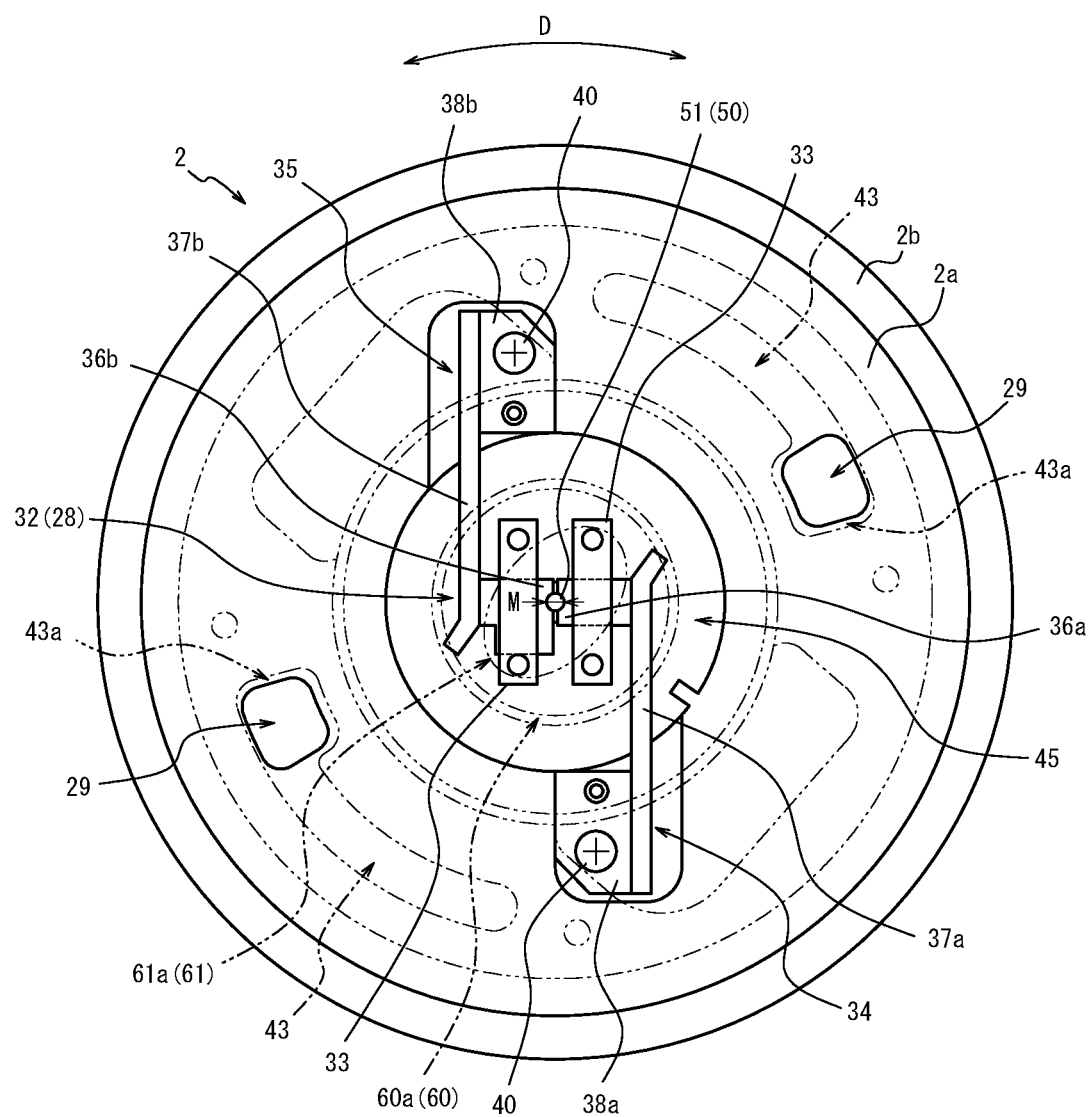
FIG. 11 illustrates an upper surface of the base plate in a state in which the base plate is detachable from the sensor insertion device.

In addition, FIG. 10 illustrates an upper surface of the base plate 2 in a state of being attached to the sensor insertion device 1, that is, in a state illustrated in FIGS. 1 to 6, and FIG. 11 illustrates the upper surface of the base plate 2 in a state of being detachable from the sensor insertion device 1, that is, in a state illustrated in FIG. 7. In FIGS. 10 and 11, the configuration of a bottom plate member constituting the bottom plate portion 3b of the housing 3 of the sensor insertion device 1 is indicated by broken lines for the sake of convenience of description.

The state where the base plate 2 is attached to the sensor insertion device 1 indicates a state where the base plate 2 and the sensor insertion device 1 cannot be separated even if the whole of the sensor insertion device 1 is moved in the pulling-out direction B with respect to the base plate 2. In addition, the state where the base plate 2 is detachable from the sensor insertion device 1 indicates a state where the base plate 2 can be separated from the sensor insertion device 1 by moving the sensor insertion device 1 in the pulling-out direction B with respect to the base plate 2.

As illustrated in FIGS. 8 to 11, the base plate 2 of the present exemplary embodiment includes a clamp portion 28 capable of clamping the sensor 50, joint portions 29 that change the engagement relationship with the bottom plate portion 3b of the housing 3 of the sensor insertion device 1 between the attached state and the detachable state of the base plate 2 and the sensor insertion device 1, a position regulating portion 30 that regulates the position of the clamp portion 28, and a adhesive portion 31 that can be stuck on the surface of the living body.

In addition, the base plate 2 of the present exemplary embodiment further includes a plate body portion 2a having a circular plate shape and a peripheral wall portion 2b formed continuously from the outer edge of the plate body portion 2a. The clamp portion 28 and the position regulating portion 30 are provided at a center portion of the upper surface of the plate body portion 2a, and the joint portions 29 are provided at outer peripheral portions of the upper surface of the plate body portion 2a. Further, the adhesive portion 31 is provided on the lower surface side of the plate body portion 2a. As illustrated in FIGS. 9 and 10, the insertion hole 70 through which the needle portion 11 (see FIGS. 1 to 7) of the sensor insertion device 1 and the sensor 50 can pass is defined in the plate body portion 2a, and the base plate 2 further includes the rubber member 71 serving as the septum which blocks the insertion hole 70 and which the needle portion 11 and the sensor 50 can pierce through and be pulled out through.

The clamp portion 28 moves, along with an operation of detaching the sensor insertion device 1 from the base plate 2 performed in the state where the sensor insertion device 1 and the base plate 2 are attached, so as to clamp the proximal end side of the sensor 50 left on the living body side after pulling out the needle member 4, the proximal end side extending to the outside of the living body. More specifically, the sensor insertion device 1 according to the present exemplary embodiment can be detached from the base plate 2 by being relatively rotated with respect to the base plate 2, and the clamp portion 28 according to the present exemplary embodiment moves, along with the rotating operation, so as to clamp the proximal end side of the sensor 50 left on the living body side after pulling out the needle member 4, the proximal end side extending to the outside of the living body.

More specifically, the clamp portion 28 of the present exemplary embodiment includes the pair of leaf spring portions 32 that clamp the proximal end side of the sensor 50 by an elastic force in a perpendicular direction C (in a state where the base plate 2 is attached to the sensor insertion device 1, a direction same as a direction perpendicular to the insertion direction A and the pulling-out direction B) perpendicular to the thickness direction of the plate body portion 2a and spring regulating portions 33 that regulate movement of the pair of leaf spring portions 32 in the thickness direction of the plate body portion 2a, and the pair of leaf spring portions 32 are configured to change the form thereof, due to the effect of the projection portion 61a having an elliptic columnar shape and serving as the cam portion 61 of the sensor insertion device 1, between a state where the sensor insertion device 1 and the base plate 2 are attached (see FIG. 10) and a state where the sensor insertion device 1 and the base plate 2 are in a detachable positional relationship (see FIG. 11). In other words, along with an operation (in the present exemplary embodiment, the operation of relatively rotating the sensor insertion device 1 with respect to the base plate 2) of detaching the sensor insertion device 1 from the base plate 2 performed in the state where the sensor insertion device 1 and the base plate 2 are attached, the projection portion 61a serving as the cam portion 61 changes the amount of elastic deformation of the pair of leaf spring portions 32 by changing the engagement relationship with the pair of leaf spring portions 32.

As illustrated in FIG. 10, the pair of leaf spring portions 32 are, in the state where the sensor insertion device 1 and the base plate 2 are attached, elastically deformed such that an opposing distance M therebetween is made longer by the projection portion 61a having an elliptic columnar shape serving as the cam portion 61. Specifically, the pair of leaf spring portions 32 are, in the state where the sensor insertion device 1 and the base plate 2 are attached, pressed to respective sides across a longitudinal direction by an outer surface of the projection portion 61a opposing in the longitudinal direction such that the pair of leaf spring portions 32 are moved away from each other, and elastically deformed such that the opposing distance M of portions clamping the sensor 50 is made longer. Therefore, the pair of leaf spring portions 32 does not clamp the sensor 50 in the state where the sensor insertion device 1 and the base plate 2 are attached (see FIG. 10).

Accordingly, a state where the opposing distance M of the pair of leaf spring portions 32 is made longer by the projection portion 61a is retained at the time of an operation of inserting the sensor 50 and the needle portion 11 and leaving the sensor 50 performed by the sensor insertion assembly 100 as illustrated in FIGS. 1 to 3, and thus the pair of leaf spring portions 32 does not come into contact with the sensor 50 and the needle portion 11. Therefore, the operation of inserting the needle portion 11 and the sensor 50 through the insertion hole 70 of the base plate 2 is not hindered by the pair of leaf spring portions 32 of the clamp portion 28.

In contrast, in the case where the sensor insertion device 1 is rotated in one direction of a circumferential direction D (see a thick arrow in FIG. 10) with respect to the base plate 2 in the state where the sensor insertion device 1 and the base plate 2 are attached (see FIG. 10), the projection portion 61a also rotates in the same direction (one direction of the circumferential direction D) with respect to the base plate 2 along with this operation. Therefore, the engagement relationship between the projection portion 61a serving as the cam portion 61 and the pair of leaf spring portions 32 changes from the state where the sensor insertion device 1 and the base plate 2 are attached (see FIG. 10).

Specifically, although the pair of leaf spring portions 32 are pressed by the outer surface of the projection portion 61a opposing in the longitudinal direction in the state where the sensor insertion device 1 and the base plate 2 are attached (see FIG. 10), the pair of leaf spring portions 32 are not in contact with the outer wall of the projection portion 61a in a state where the base plate 2 is moved to the position at which the base plate 2 can be detached from the sensor insertion device 1 (see FIG. 11) by rotating the sensor insertion device 1 in one direction of the circumferential direction D with respect to the base plate 2. That is, the pair of leaf spring portions 32 are released from the pressure applied by the projection portion 61a and are moved by the restoring force so as to be closer to each other in the perpendicular direction C, and thus the opposing distance M becomes short compared with in the state where the sensor insertion device 1 and the base plate 2 are attached (see FIG. 10). The pair of leaf spring portions 32 of the clamp portion 28 can clamp the proximal end side of the sensor 50 extending to the outside of the living body by the restoring force. In the present exemplary embodiment, the optical fiber 51 of the sensor 50 is clamped by the pair of leaf spring portions 32.

That is, when separating the sensor 50 and the base plate 2 from the sensor insertion device 1 and leaving the sensor 50 and the base plate 2 on the living body side (see FIG. 7) after inserting the sensor 50 and the needle portion 11 (see FIGS. 1 and 2) and pulling out the needle portion 11 (see FIG. 3) are completed by the sensor insertion assembly 100, the clamp portion 28 of the base plate 2 clamps the sensor 50 along with a detaching operation from the sensor insertion device 1. Accordingly, the base pate 2, whose position is fixed on the surface of the living body by the adhesive portion 31 that will be described later after detachment of the sensor insertion device 1, clamps the portion of the sensor 50 extending to the outside of the living body, and thus movement of the portion of the sensor 50 left in the living body to be pulled out of the living body due to body movement or the like of the person to be measured can be suppressed.

More specifically, the pair of leaf spring portions 32 of the present exemplary embodiment includes a first leaf spring 34 and a second leaf spring 35 disposed so as to oppose the first leaf spring 34, and the first leaf spring 34 and the second leaf spring 35 are attached to an upper surface of the plate body portion 2a. The first leaf spring 34 includes an abutting portion 36a that abuts and presses the sensor 50 when clamping the sensor 50, a deformation portion 37a that is integral with or connected to the abutting portion 36a and capable of changing the position of the abutting portion 36a in the perpendicular direction C by being elastically deformed, and a fixing portion 38a that fixes a first end of the deformation portion 37a to the plate body portion 2a. In addition, the second leaf spring 35 also includes an abutting portion 36b, a deformation portion 37b, and a fixing portion 38b similarly to the first leaf spring 34.

The abutting portions 36a and 36b each include a recess portion 39 that receives the sensor 50 when clamping the sensor 50. The recess portion 39 of each of the abutting portions 36a and 36b has an approximately semicircular shape when the base plate 2 is viewed from the upper surface side (see FIGS. 10 and 11), and the sensor 50 is clamped by the recess portions 39 of the abutting portions 36a and 36b. In the present exemplary embodiment, a distance between points corresponding to bottom positions of the recess portions 39 of the abutting portions 36a and 36b having semicircular shapes when the base plate 2 is viewed from the upper surface side is set as the opposing distance M described above (see FIGS. 10 and 11).

As illustrated in FIGS. 8 to 11, the deformation portion 37a is a long plate-shaped member a first end of which is continuous with the abutting portion 36a and the second end of which is continuous with the fixing portion 38a, and the first end side of the deformation portion 37a continuous with the abutting portion 36a is capable of being elastically deformed by using the position of the fixing portion 38a fixed to the plate body portion 2a by a positioning portion 47 of the plate body portion 2a and a screw 40 as a supporting point. Therefore, the position of the abutting portion 36a in the nonstop direction C (see FIG. 1, etc.) can be changed by elastically deforming the first end side of the deformation portion 37a continuous with the abutting portion 36a. With regard to this point, the same applies to the deformation portion 37b and the fixing portion 38b of the second leaf spring 35.

The spring regulating portions 33 are configured to regulate the movement of the pair of leaf spring portions 32 in the thickness direction of the plate body portion 2a, and the spring regulating portions 33 of the present exemplary embodiment are constituted by rectangular plate members. In addition, the spring regulating portions 33 of the present exemplary embodiment are attached and fixed to the upper surface of the plate body portion 2a in a state where the spring regulating portions 33 are respectively in contact with the upper surfaces of the abutting portions 36a and 36b so as to respectively cover the upside of the abutting portion 36a of the first leaf spring 34 and the abutting portion 36b of the second leaf spring 35. Specifically, the spring regulating portions 33 are fixed to the plate body portion 2a by firmly engaging fixing projections 46 formed on the upper surface of the plate body portion 2a with fixing holes defined in the spring regulating portions 33 in the presence of the abutting portions 36a and 36b between the spring regulating portions 33 and the plate body portion 2a (see FIGS. 8 and 9).

An accommodation recess portion 45 that accommodates the pair of leaf spring portions 32 and the spring regulating portions 33 is defined in the center of the upper surface of the plate body portion 2a of the present exemplary embodiment.

The joint portions 29 regulate the movement of the sensor insertion device 1 in the pulling-out direction B with respect to the base plate 2 by engaging with the bottom plate portion 3b (see FIG. 1, etc.) of the sensor insertion device 1 in the state where the base plate 2 is attached to the sensor insertion device 1 (see FIG. 10). In addition, the joint portions 29 permit the movement of the sensor insertion device 1 in the pulling-out direction B with respect to the base plate 2 by not engaging with the bottom plate portion 3b of the sensor insertion device 1 in the state where the base plate 2 is at a position at which the base plate 2 is detachable from the sensor insertion device 1 (see FIG. 11).

Specifically, as illustrated in FIG. 8, the joint portions 29 of the present exemplary embodiment each include a trunk portion 41 provided so as to project upward (in the state where the base plate 2 is attached to the sensor insertion device 1, in the same direction as the pulling-out direction B) from the upper surface of the plate body portion 2a and a distal end portion 42 that is formed so as to be continuous from the trunk portion 41, is crooked at the distal end of the trunk portion 41 and extends in the nonstop direction C.

By moving the trunk portions 41 and the distal end portions 42 in joint holes 43 defined in the bottom plate member constituting the bottom plate portion 3b and in recess portions 44 (see FIG. 1 and so forth) that are defined in the lower surface of a flange portion 62 of a housing body, which constitutes the bottom plate member together with the bottom plate portion 3b, and that communicate with the joint holes 43, the attached state and detachable state of the sensor insertion device 1 and the base plate 2 can be switched.

The joint holes 43 formed in the bottom plate member constituting the bottom plate portion 3b (see FIG. 1, etc.) each have a shape long in the circumferential direction D when the bottom plate member is viewed from the upper surface side (see broken lines in FIGS. 10 and 11), and each include, at a first end in the circumferential direction D, an attachment/detachment opening portion 43a in which and from which the trunk portion 41 and the distal end portion 42 are inserted and pulled out in attachment and detachment of the base plate 2. The attachment/detachment opening portion 43a has a large width (length in the radial direction in FIGS. 10 and 11) compared with other portions of the joint hole 43. In addition, as illustrated in FIGS. 10 and 11, the length of the joint portion 29 in the radial direction of the base plate 2 when the base plate 2 is viewed from the upper surface side (in the present exemplary embodiment, equal to the length of the distal end portion 42) is smaller than the width of the attachment/detachment opening portion 43a of the joint hole 43 and is larger than the width of the portions of the joint hole 43 other than the attachment/detachment opening portion 43a.

In addition, as illustrated in FIG. 1, the recess portions 44 defined in the flange portion 62 cover the upside of the joint holes 43 of the bottom plate member and each have a shape long in the circumferential direction D similarly to the joint holes 43. Further, the recess portions 44 each have a width approximately equal to the attachment/detachment opening portion 43a, that is, a width larger than the length of the joint portions 29 in the radial direction of the base plate 2 when the base plate 2 is viewed from the upper surface side, regardless of the position in the circumferential direction D.

Therefore, when joining the sensor insertion device 1 and the base plate 2 (see FIG. 7) that are separated from each other, the distal end portions 42 of the joint portions 29 of the base plate 2 are inserted in the attachment/detachment opening portions 43a of the joint holes 43. Then, after the distal end portions 42 reach the positions of the recess portions 44, the distal end portions 42 of the joint portions 29 move in the recess portions 44 and the trunk portions 41 of the joint portions 29 move in the joint holes 43 in the circumferential direction D by rotating one of the base plate 2 and the sensor insertion device 1 in the circumferential direction D with respect to the other. As a result of the rotating operation, the positions of the joint portions 29 and the attachment/detachment opening portions 43a are displaced in the circumferential direction D. Therefore, when it is attempted to move the sensor insertion device 1 in the pulling-out direction B with respect to the base plate 2, the distal end portions 41 of the joint portions 29 abut and thereby interfere with the bottom plate portion 3b, and thus the movement of the sensor insertion device 1 in the pulling-out direction B is regulated by the joint portions 29. That is, this state is the state where the base plate 2 is attached to the sensor insertion device 1 (see FIG. 10).

Conversely, when separating the sensor insertion device 1 and the base plate 2 from each other in the state where the sensor insertion device 1 and the base plate 2 are attached (see FIG. 10), one of the base plate 2 and the sensor insertion device 1 is rotated in the circumferential direction D with respect to the other to cause the positions of the joint portions 29 and the attachment/detachment opening portions 43a to coincide with each other in the circumferential direction D. Accordingly, the movement of the sensor insertion device 1 in the pulling-out direction B with respect to the base plate 2 is no longer regulated by the joint portions 29 because the distal end portions 41 of the joint portions 29 do not abut and thus not interfere with the bottom plate portion 3b. That is, this state is the state where the base plate 2 is at a position at which the base plate 2 is detachable from the sensor insertion device 1 (see FIG. 11). When separating the sensor insertion device 1 and the base plate 2 after leaving the sensor 50 in the living body, the sensor insertion device 1 is moved to the position where the sensor insertion device 1 is detachable from the base plate 2 via an operation of rotating the sensor insertion device 1 with respect to the base plate 2 in a state where the base plate 2 is pressed against the surface of the living body. Accordingly, according to the sensor insertion assembly 100 of the present exemplary embodiment, a patient or a health care worker can perform, by operating one hand holding the sensor insertion device 1, a series of operations including pressing the base plate 2 against the surface of the living body, rotating the sensor insertion device 1 with respect to the base plate 2, and moving the sensor insertion device 1 in the pulling-out direction B to separate the sensor insertion device 1 from the base plate 2.

In the present exemplary embodiment, the attached state (see FIG. 10) and detachable state (see FIG. 11) of the sensor insertion device 1 and the base plate 2 can be switched by relatively rotating one of the sensor insertion device 1 and the base plate 2 with respect to the other in the circumferential direction D and changing the positional relationship between the attachment/detachment opening portions 43a of the sensor insertion device 1 and the joint portions 29 of the base plate 2 in the circumferential direction D. In addition, as described above, the engagement relationship between the pair of leaf spring portions 32 and the cam portion 61 (in the present exemplary embodiment, the projection portion 61a) changes along with the switching, and thus the sensor 50 can be clamped by the elastic force of the pair of leaf spring portions 32 by switching the state where the sensor insertion device 1 and the base plate 2 are attached to the state where these two are detachable.

As described above, in the present exemplary embodiment, as a result of performing the rotating operation for separating the sensor insertion device 1 from the base plate 2 in the pulling-out direction B after inserting the sensor 50 in the living body by using the sensor insertion assembly 100, the pair of leaf spring portions 32 of the clamp portion 28 of the base plate 2 that move along with the rotating operation clamp the sensor 50 by an elastic force. However, the specific configuration for realizing the attachment and detachment of a sensor insertion device and a base plate by relative rotating between these two and the specific configuration of a clamp portion that clamps a sensor along with the rotating operation for detaching the base plate from the sensor insertion device are not limited to the configuration of the present exemplary embodiment, and can be realized by various configurations, for example, by using screw connection for the attachment and detachment of the sensor insertion device and the base plate or using a moving member that moves without deformation and clamps the sensor along with the rotating operation for detaching the base plate from the sensor insertion device. In addition, although an operation of rotating one of the sensor insertion device 1 and the base plate 2 with respect to the other is performed as the operation for separating the sensor insertion device 1 from the base plate 2, and the clamp portion 28 that operates along with the rotating operation is used in the present exemplary embodiment, for example, a clamp portion that clamps the sensor along with an operation of moving the sensor insertion device in the pulling-out direction with respect to the base plate may be used. However, since it is not required to secure an operation distance (in the present exemplary embodiment, the length of the joint holes 43 in the circumferential direction D) for switching the attached state and detachable state of the sensor insertion device and the base plate in the thickness direction of the base plate as a result of using a clamp portion that operates along with the rotating operation as in the present exemplary embodiment, it becomes easy to design the base plate whose thickness in the pulling-out direction is thinner compared with the case where the clamp portion is configured to operate along with the movement of the sensor insertion device in the pulling-out direction.

The sensor insertion device 1 separated from the base plate 2 after leaving the sensor 50 is configured such that a user does not touch the distal end of the needle portion 11. Specifically, the distal end of the needle portion 11 is accommodated in the housing 3 so as not to project to the outside from the bottom plate portion 3b of the housing 3 (see FIGS. 3, 6, and 7).

Figure 12:
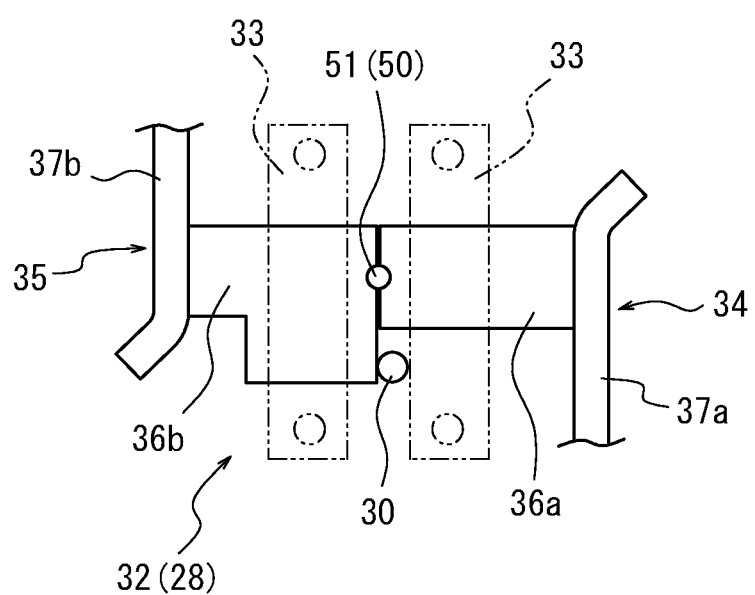
FIG. 12 is an enlarged view of a center portion of the base plate illustrated in FIG. 11.

FIG. 12 is an enlarged view of a center portion of the base plate 2 illustrated in FIG. 11. The second leaf spring 35 described above is configured to have a larger spring constant than the first leaf spring 34, and, as illustrated in FIG. 12, the base plate 2 includes a positioning pin serving as the position regulating portion 30 that regulates the position of the second leaf spring 35 when detaching the sensor insertion device 1. The positioning pin is omitted in FIGS. 8 to 11 for the sake of convenience of description. In addition, in FIG. 12, the spring regulating portions 33 are indicated by broken lines for the sake of convenience of description.

The positioning pin serving as the position regulating portion 30 is provided so as to project from the upper surface of the plate body portion 2a, and abuts the abutting portion 36b of the second leaf spring 35 that moves so as to clamp the sensor 50 to regulate further movement of the abutting portion 36b of the second leaf spring 35 when detaching the sensor insertion device 1 and the base plate 2, that is, when performing an operation (see FIG. 10) of rotating the sensor insertion device 1 in the circumferential direction D with respect to the base plate 2 in the state where the sensor insertion device 1 and the base plate 2 are attached. That is, the second leaf spring 35 having a larger spring constant than the first leaf spring 34 is positioned by the positioning pin, and the sensor 50 is clamped between the first leaf spring 34 and the second leaf spring 35 as a result of the first leaf spring 34 being pressed against the second leaf spring 35 positioned by the positioning pin.

As described above, since a configuration in which the spring constant of the second leaf spring 35 is larger than the spring constant of the first leaf spring 34 and the second leaf spring 35 is positioned by causing the second leaf spring 35 to the position regulating portion 30 is employed in the present exemplary embodiment, the sensor 50 clamped between the first leaf spring 34 and the second leaf spring 35 can be clamped by the abutting portion 36a of the first leaf spring 34 and the abutting portion 36b of the second leaf spring 35 at a position of the recess portion 39 (see FIG. 9) of the abutting portion 36b of the second leaf spring 35 abutting the position regulating portion 30. That is, since second leaf spring 35 that abuts the position regulating portion 30 functions to position the sensor 50 to be clamped, the variation of the clamping position of the sensor 50 on the base plate 2 can be suppressed. Particularly, in a sensor using an optical fiber, precise biological information can be obtained by suppressing the variation of the clamping position of the sensor because signals are changed by slight movement of the optical fiber left in the living body.

The adhesive portion 31 is provided on a surface opposing the surface of the living body, that is, the lower surface, of the base plate 2 so as to adhere on the surface of the living body such that the position of the base plate 2 on the surface of the body is less likely to be changed when inserting the sensor 50 by using the sensor insertion assembly 100 and being separated from the sensor insertion device 1 and left on the surface of the living body.

The adhesive portion 31 of the present exemplary embodiment is constituted by a double-sided adhesive sheet including a first adhesive layer that adheres on the lower surface of the base plate 2 and a second adhesive layer that adheres on the surface of the living body, but is not limited to this configuration. For example, the adhesive portion 31 maybe configured in various ways such as by simply providing an adhesive on the lower surface of the base plate 2 at positions other than the insertion hole 70 to configure the adhesive portion 31. In addition, in the case of configuring the adhesive portion 31 by the double-sided adhesive sheet, a configuration in which the adhesive portion 31 is provided on the whole area of the lower surface of the base plate 2 and is pierced through at the position of the insertion hole 70 when inserting the sensor 50 and the needle portion 11 by using the sensor insertion assembly 100 may be employed, and a configuration in which the adhesive portion 31 is stuck on the other part than the insertion hole 70 on the lower surface of the base plate 2 may be alternatively employed.

As the adhesive used for the adhesive portion 31 that comes into contact with the surface of the living body, for example, adhesives such as rubber-based adhesives, acrylic adhesives, and silicone-based adhesives may be used.

In addition, the other portions of the base plate 2 than the adhesive portion 31 may be formed from the same material as the housing 3 of the sensor insertion device 1 described above.

As described above, the sensor insertion assembly 100 of the present exemplary embodiment includes the sensor insertion device 1 that accommodates the needle member 4 that is inserted in the living body with the sensor 50 capable of detecting biological information and is pulled out of the living body after leaving the distal end side of the sensor 50 in the living body and the base plate 2 that is detachably attached to the sensor insertion device 1, and the base plate 2 is separated from the sensor insertion device 1 and left on the living body side with the sensor 50 after leaving the sensor 50 in the living body. Moreover, the processing device capable of processing the biological information of the person to be measured detected by the sensor 50 is attached to the base plate 2 left on the surface of the living body, and it becomes possible to, for example, monitor temporal change in the blood glucose level of a diabetic patient for a predetermined period on the basis of the biological information of the person to be measured.

The sensor insertion assembly and the base plate according to the present invention are not limited to the configuration of the exemplary embodiment described above, and may be realized by various configurations within the scope of what is described in Claims. For example, for the sensor insertion device 1, although the movable member 7 is used as a plunger that is moved by the elastic force of the insertion spring 5a in insertion of the sensor 50 and the needle portion 11 in the living body, the movable member 7 may be configured to not be moved in insertion of a sensor and a needle portion performed by the urging force of a first urging member and to be moved in pulling out of the needle portion performed by the urging force of the second urging member.

The present disclosure relates to a sensor insertion assembly including a sensor insertion device and a base plate and to the base plate, the sensor insertion device being configured to insert a sensor that detects biological information of a living body such as a patient in the living body.

REFERENCE NUMERAL LIST

1 sensor insertion device
2 base plate
2a plate body portion
2b peripheral wall portion
3 housing
3a cylinder portion
3b bottom plate portion
3c top plate portion
4 needle member
5 first urging member
5a insertion spring (first elastic member)
6 second urging member
6a retrieving spring (second elastic member)
7 movable member
7a cylinder portion
7b flange portion
7c deformation portion
7d top plate portion
8 operation member
9 insertion hole of bottom plate portion
10 insertion hole of top plate portion
11 needle portion
12 connection portion
13 locked portion
14 insertion hole of connection portion
15 locking claw portion (locking portion)
16 receiving portion
17 connection portion
18 projection portion (locking portion)
19 rod portion
20 cutout
21 claw
22 projection
22a lower surface of projection
23 pressing plate portion
24 claw
25 projection portion
26 pressing portion
27 tapered portion
28 clamp portion
29 joint portion
30 position regulating portion
31 adhesive portion
32 pair of leaf spring portions
33 spring regulating portion
34 first leaf spring
35 second leaf spring
36a, 36b abutting portion
37a, 37b deformation portion
38a, 38b fixing portion
39 recess portion
40 screw
41 trunk portion
42 distal end portion
43 joint hole 43a attachment/detachment opening portion
44 recess portion
45 accommodation recess portion
46 fixing projection
47 positioning portion
50 sensor
51 optical fiber
60 engagement portion (locking release portion)
60a projection portion
61 cam portion
61a projection portion
62 flange portion
70 insertion hole
71 rubber member
100 sensor insertion assembly
A insertion direction
B pulling-out direction
C direction perpendicular to thickness direction of plate body portion
D circumferential direction
M opposing distance
O center axis line

What is claimed is:

1. A sensor insertion assembly comprising:
a sensor insertion device comprising a needle member configured to be inserted in a living body together with a biological information sensor and to be pulled out of the living body after leaving a distal end side of the sensor in the living body; and
a base plate detachably attached to a first end side of the sensor insertion device, the base plate comprising a clamp portion configured to move so as to clamp a proximal end side of the sensor extending to an outside of the living body after pulling out the needle member and along with an operation of detaching the sensor insertion device from the base plate,
wherein the sensor insertion device is detachable from the base plate by being rotated with respect to the base plate.

2. The sensor insertion assembly according to claim 1, wherein the clamp portion includes first and second leaf springs configured to clamp the proximal end side of the sensor, and
wherein the sensor insertion device includes a cam portion configured to change an engagement relationship with the first and second leaf springs along with rotation of the sensor insertion device with respect to the base plate, and thereby change an amount of elastic deformation of the first and second leaf springs.

3. The sensor insertion assembly according to claim 2, wherein:
the second leaf spring is disposed so as to oppose the first leaf spring,
a spring constant of the second leaf spring is larger than a spring constant of the first leaf spring, and
the base plate includes a position regulating portion configured to regulate a position of the second leaf spring when the base plate is detached from the sensor insertion device.

4. The sensor insertion assembly according to claim 3, wherein:
an adhesive portion is disposed on a surface of the base plate, the adhesive being adapted to adhere to the human body during use of the sensor insertion assembly.

5. The sensor insertion assembly according to claim 4, wherein the sensor comprises:

a detection portion configured to be left in the living body and configured to detect biological information, and
an optical fiber,
wherein the detection portion is attached to a distal end portion of the optical fiber, and
wherein the optical fiber is configured to extend from the detection portion to a location outside the living body during use of the sensor.

6. The sensor insertion assembly according to claim 3, wherein the sensor comprises:
a detection portion configured to be left in the living body and configured to detect biological information, and
an optical fiber,
wherein the detection portion is attached to a distal end portion of the optical fiber, and
wherein the optical fiber is configured to extend from the detection portion to a location outside the living body during use of the sensor.

7. The sensor insertion assembly according to claim 2, wherein:
an adhesive portion is disposed on a surface of the base plate, the adhesive being adapted to adhere to the human body during use of the sensor insertion assembly.

8. The sensor insertion assembly according to claim 7, wherein the sensor comprises:
a detection portion configured to be left in the living body and configured to detect biological information, and
an optical fiber,
wherein the detection portion is attached to a distal end portion of the optical fiber, and
wherein the optical fiber is configured to extend from the detection portion to a location outside the living body during use of the sensor.

9. The sensor insertion assembly according to claim 2, wherein the sensor comprises:
a detection portion configured to be left in the living body and configured to detect biological information, and
an optical fiber,
wherein the detection portion is attached to a distal end portion of the optical fiber, and
wherein the optical fiber is configured to extend from the detection portion to a location outside the living body during use of the sensor.

10. The sensor insertion assembly according to claim 1, wherein:
an adhesive portion is disposed on a surface of the base plate, the adhesive being adapted to adhere to the human body during use of the sensor insertion assembly.

11. The sensor insertion assembly according to claim 10, wherein the sensor comprises:
a detection portion configured to be left in the living body and configured to detect biological information, and
an optical fiber,
wherein the detection portion is attached to a distal end portion of the optical fiber, and
wherein the optical fiber is configured to extend from the detection portion to a location outside the living body during use of the sensor.

12. The sensor insertion assembly according to claim 1, wherein the sensor comprises:
a detection portion configured to be left in the living body and configured to detect biological information, and
an optical fiber,
wherein the detection portion is attached to a distal end portion of the optical fiber, and wherein the optical fiber is configured to extend from the detection portion to a location outside the living body during use of the sensor.

\* \* \* \* \*